United States Patent [19]

Mislick

[11] Patent Number: 5,783,566
[45] Date of Patent: Jul. 21, 1998

[54] METHOD FOR INCREASING OR DECREASING TRANSFECTION EFFICIENCY

[75] Inventor: Kimberly Ann Mislick, Los Angeles, Calif.

[73] Assignee: California Institute of Technology, Pasadena, Calif.

[21] Appl. No.: 644,095

[22] Filed: May 10, 1996

Related U.S. Application Data

[60] Provisional application No. 60/013,647 Mar. 18, 1996.
[51] Int. Cl.⁶ .................... A61K 38/00; A61K 48/00; C12N 5/00; C12N 15/00
[52] U.S. Cl. ................ 514/44; 514/1; 514/2; 435/172.1; 435/325; 424/450; 935/52; 935/54
[58] Field of Search .................. 514/7, 44, 8, 56, 514/2, 1; 424/450; 552/544; 935/52, 54; 530/395; 435/172.1, 325

[56] References Cited

U.S. PATENT DOCUMENTS

| | | | |
|---|---|---|---|
| 5,108,921 | 4/1992 | Low et al. | 435/240.1 |
| 5,264,618 | 11/1993 | Felgner et al. | 560/224 |
| 5,459,127 | 10/1995 | Felgner et al. | 514/7 |
| 5,635,380 | 6/1997 | Naftilan et al. | 435/172.3 |

FOREIGN PATENT DOCUMENTS

| | | |
|---|---|---|
| WO 91/06309 | 5/1991 | WIPO. |
| WO 93/03709 | 3/1993 | WIPO. |
| WO 93/14778 | 8/1993 | WIPO. |

OTHER PUBLICATIONS

Ciccarone et al., *Focus* 15:73–83 (1992).
Christiano et al., *Proc. Natl. Acad. Sci. USA* 90:2122–26 (1993).
Conget and Minguell, *Br. J. Harmatology* 89:1–7 (1995).
Cotton et al., *Methods in Enzymology* 217:618–645 (1993).
Felgner and Ringold, *Nature* 337:387–388 (1989).
Fransson, *TIBS* 12:406–411 (1987).
Gao et al., *Human Gene Therapy* 4:17–24 (1993).
Grassel et al., *Molecular and Cellular Biochem* 145:61–68 (1995).
Guy et al., *Molecular Biotechnology* 3:237–248 (1995).
Harrison et al., *BioTechniques* 19:816–823 (1995).
Jackson et al., *Physiological Reviews* 71(2):481–533 (1991).
Nietfeld, *Experientia* 49:456–468 (1993).
Timar et al., *Int. J. Cancer* 62:755–761.
Yoshimura et al., *Journal of Biological Chemistry* 268:2300–2303 (1993).
Wang et al (1987) *Proc. Natl. Acad. Sci. USA* 84: 7851–7855.
Miller et al (1995) *FASEB J.* 9: 190–199.
Marshall, E (1995) *Science* 269:1050–1055.

*Primary Examiner*—Bruce R. Campbell

[57] ABSTRACT

Methods for controlling transfection efficiency mediated by complexes of cationic species and genetic material by adjusting the amount of membrane-associated proteoglycans and optionally adjusting the plasma concentration of glycosaminoglycans. Transfection efficiency is controlled by the amount of membrane-associated proteoglycans in the cell to be transfected and also by the plasma concentration of glycosaminoglycans. By increasing the amount of membrane-associated proteoglycans in the cell, and optionally decreasing the plasma concentration of glycosaminoglycans, the transfection efficiency can be increased. By decreasing the amount of membrane-associated proteoglycans in the cell, and optionally decreasing the plasma concentration of glycosaminoglycans, the transfection efficiency can be decreased. Transfection efficiency can be controlled, whether performed in vivo, ex vivo, or in vitro.

37 Claims, 5 Drawing Sheets

METHOD FOR INCREASING OR DECREASING TRANSFECTION EFFICIENCY

This application claims priority under 35 USC §119 from U.S. patent application Ser. No. 60/013,647, filed Mar. 18, 1996, entitled "Methods for Increasing or Decreasing Transfection Efficiency".

FIELD OF THE INVENTION

This invention is in the field of transfection of cells with genetic material, and relates to methods for increasing or decreasing transfection efficiency. During transfection, the genetic material may be introduced into the cell to correct a functional cellular defect, to augment an immune response or to express a foreign protein. When transfection is inhibited, the inhibition may be inhibition of viral infection or minimization of transfection at a non-desired site. The transfection efficiency can be controlled in vivo, ex vivo and in vitro.

BACKGROUND OF THE INVENTION

Gene transfer is a term that broadly encompasses methods for introducing exogenous gene sequences into a cell or group of cells. There are a variety of methods known to those of skill in the art for introducing exogenous genetic material into a host cell. These methods include, but are not limited to, calcium precipitation, viral vector-mediated delivery, electroporation, and complexing the DNA with a cationic substance. Such cationic substances include, but are not limited to, cationic lipids such as lipofectin and DOTMA (N-[1-(2,3-dioleyloxy)propyl]N,N,N-trimethylammonium), cationic liposomes prepared from cationic lipids, cationic polyamino acids such as poly-L-lysine and polyornithine, cationic amphiphiles, polyethyleneimine, dendrite polymers with cationic substituents, and DEAE-dextran.

Gene transfer in vitro may be used to study the effect of a given gene and its resulting gene product on a given population of cells. Gene transfer is typically directed to the areas of gene replacement and augmentation. Gene augmentation introduces a correct copy of a mutated gene into defective cells or a copy of a foreign sequence for gene expression within that cell. Gene replacement corrects defective genetic sequences, permitting targeted homologous recombination for a known gene sequence. Both approaches generally require that the exogenous genetic material, for example, polynucleotide sequences, be stably expressed, rather than being transiently expressed.

Genes can also be introduced that make cells chemosensitive. In some cases, a disease is encoded by multiple, discontinuous genes. In this case, replacing a single gene is unlikely to lead to eradication of the disease. However, a "suicide" gene may be transfected to induce the self-destruction of diseased cells and tissues. This approach is currently being developed to treat a number of cancers. In one strategy, target tissues are transfected with the Herpes Simplex Virus-thymidine kinase (HSV-tk) gene and then treated with gancyclovir, a nucleotide analog. Phosphorylated gancyclovir produced by transfected cells is incorporated into genomic DNA and further elongation is prevented. This mode of treatment is enhanced by the "by-stander effect" i.e., the passage of phosphorylated gancyclovir into neighboring non-transduced cells through gap junctions. Thus, the growth of the tumor is inhibited by transfecting only a fraction of the tumor mass. In this type of gene transfer, expression can be either stable or transient.

Examples of stable transfectants selected for gene therapy directed to skeletal muscle and hematopoietic cells are found in publications by Salminen et al. and Dick et al. (Hum. Gene Ther. 2:15-26, 1991 and Blood 78:624-634, 1991 respectively) which are hereby incorporated by reference. Stable expression is thought to require either stable integration or homologous recombination of DNA in the transfected cell.

Gene therapy may involve either in vivo delivery of the gene sequence to the targeted tissue, or removal of targeted tissue, ex vivo transfection, and return of the targeted tissue. A major challenge to in vivo gene therapy is the effective delivery of the gene sequence to the targeted tissue and sufficient transfection in vivo. The efficacy of gene therapy for in vivo applications is limited by the accessibility of the gene to the target cells, the ability to transfect only those cells in need of transfection, and the presence of components in the body that interfere with transfection.

In some embodiments, genetic material, such as modified and un-modified DNA and RNA sequences, is not used for gene replacement or augmentation, but for binding to or interacting with various sites. The identification and use of such oligomers is referred to as the SELEX process, and the oligomers identified by the process are referred to as SELEX oligomers. The SELEX process and SELEX oligomers are described in U.S. Pat. No. 5,270,163, the contents of which are hereby incorporated by reference. Uses for the oligomers include in vitro diagnostic applications and in vivo or ex vivo therapeutic applications.

Ex vivo gene augmentation or gene replacement involves removing cells from a patient, optionally expanding these cells in culture, transfecting the cells and identifying stable transfectants. After stable transfectants are identified, the cells are optionally expanded and returned to the host. This procedure has been used most successfully to transfect cells of hematopoietic origin.

Other cell types that have been stably transfected in culture include fibroblasts, myoblasts and hepatocytes. Stable cell lines have been used experimentally for certain applications in place of autologous host cells. These procedures require that the cells are maintained in culture. A major limitation of in vitro expansion before transfection and the selection of stably transfected cells following transfection is the length of time the cells spend in culture. The time required to obtain cells from a patient, treat the cells, select stable transfectants and return these to their host can be a matter of weeks to months. In the absence of the in vivo cellular milieu, protein expression may change. Over time, certain subpopulations of cells survive under selection conditions and replicate better than others. The conditions used to select stable transfectants also selects for cells able to survive in culture. Cell survival in vitro does not necessarily translate into improved cell survival in vivo. Cells adapted to culture or cells expanded in culture may not be able to survive in vivo. A method that minimizes cell time in culture, i.e., by increasing the transfection efficiency, may reduce the likelihood that cell changes occur in vitro.

Time constraints are not as critical in in vivo transfection. However, it is often difficult to effectively target gene therapy to the desired cells, and conditions that work in vitro often do not work in vivo, resulting in lower transfection efficiency, or no transfection of the desired cells at all. Since genetic material is extremely expensive and difficult to prepare, it is important to maximize transfection efficiency, whether performed in vitro, in vivo, or ex vivo.

Several methods for improving in vivo and ex vivo transfection have been investigated to overcome the problems associated with these approaches. A number of gene delivery agents have been developed that increase the transfection efficiency both in vitro and ex vivo. The majority of these agents are cationic, amine-based macromolecules that form stable complexes with DNA. Although these gene delivery agents have shown some success, the mechanism by which they increase transfection efficiency has been poorly understood.

One type of widely studied gene delivery agent is a cationic lipid or a cationic liposome. Various cationic lipids such as DOTMA have been shown to interact spontaneously with DNA to form lipid:DNA complexes that purportedly fuse with negatively charged lipids associated with cell membranes (Felgner, P. L. et al., Proc. Natl. Acad. Sci. (USA) 84:7413–7417 (1987) and U.S. Pat. No. 4,897,355 to Eppstein, D. et al.). Complexes of genetic material and cationic species, for example, cationic lipids and liposomes prepared from the cationic lipids, have been described in PCT WO 93/14778 by Felgner et al., the contents of which are hereby incorporated by reference. It is believed that complexing DNA with cationic lipids or cationic liposomes renders the DNA resistant to nuclease activity (Huang, Biochemistry, 35(3):1027–1036 (January 1996)).

Cationic liposomes have been used in vitro to introduce genetic sequences into tissue culture cells (Mannino, R. J., Fould-Fogerite, S., Biotechniques 6:682–690, 1988). Liposome-mediated gene delivery can deliver mRNA, RNA, DNA, a modified polynucleotide or oligonucleotide, or a combination thereof directly into the cell cytoplasm (Malone et al., Proc. Natl. Acad. Sci. (USA) 86:6077–6081, (1989)).

Variables thought to affect the efficiency of gene expression include the type of lipid in the cationic liposomes, the relative amounts of DNA and lipid, the day of assay following transfection, the media used for lipid:DNA complex formation, the promoter driving expression observed with the reporter gene, the physiological state of the cells (e.g., whether or not the cells were differentiated) and the type of cell. Maximal expression in transfected primary cells was one to two orders of magnitude lower than with cell lines (Harrison et al., Biotechniques, 19(5):816–823 (November 1995)).

Research devoted to developing gene delivery agents has significantly improved in vitro transfection efficiency. However, the interactions between these agents and their target cells remain largely uncharacterized. Several mechanisms have been proposed for how the genetic material enters the cell. These mechanisms include entry through the plasma membrane (Legendre and Szoka, Proc. Natl. Acad. Sci. U.S.A., 90(3):893–897 (1993)) and delivery via endocytosis (Legendre and Szoka, Pharm. Res. 9(10):1235–1242 (1992)).

There has been considerable interest in defining the molecular mechanisms by which proteoglycans and glycosaminoglycans regulate cell growth and differentiation. The role is believed to be an intracellular effect, rather than an extracellular effect (Jackson, et al., "Glycosaminoglycans," Physiological Reviews, 71(2):481–533 (1991)). While acknowledging that additional studies are necessary, Jackson indicated that membrane vesicle mediated transport is depressed during mitosis. In Chinese hamster ovary (CHO) cells, there is a dramatic decrease in the incorporation of sulfate into glycosaminoglycans when the cells enter the mitotic phase. After mitosis, heparan sulfate proteoglycans are taken up by the cells and heparan sulfate appears in the nucleus. It has been postulated that glycosaminoglycans deliver growth factor to the nucleus to enhance gene expression (Jackson, supra, at 520).

Sulfated proteoglycans are among the most negatively charged components of the cell. They consist of a core protein covalently linked to one or more of four types of sulfated glycosaminoglycans. Heparin and heparan sulfate are the most anionic glycosaminoglycans, followed by dermatan sulfate, chondroitan sulfate, and keratan sulfate. Although most well-known for their structural contribution to basement membranes and the extracellular matrix, proteoglycans participate in a variety of cellular events as membrane-bound proteins. Membrane-associated heparan sulfate proteoglycans mediate infection by the Herpes Simplex Virus and the binding of low-density lipoprotein and epidermal growth factor. Chondroitan sulfate proteoglycans promote the attachment of human foreskin fibroblasts to cationic diamine derivatized glass. Moreover, cellular proteoglycans bind to gold-labeled polylysine, a technique used to localize them by electron microscopy. However, the role of proteoglycans and glycosaminoglycans in cationic liposome-mediated transfection has not been extensively studied.

It has been proposed that certain plasma components inhibit cationic liposome-mediated transfection (Felgner and Ringold, Nature, 337:26 (1989)). Felgner suggests that sulfated proteoglycans and similar polyvalent negatively charged serum components may be responsible for this effect. Felgner does not suggest that the mechanism of transfection involves any interaction with these species present on the cell surface.

Better characterization of the mechanism by which transfection is mediated by complexes of cationic species and genetic material leads to the design of improved methods and agents for gene delivery and could help explain the variable transfection efficiency observed among different cell types, and in in vivo versus in vitro or ex vivo transfection. Better characterization of the transfection mechanism also leads to the design of improved methods and agents for inhibiting viral infection.

Non-differentiated cells are extremely difficult to transfect. However, because these cells are non-differentiated, it would be extremely advantageous to transfect such cells. For example, treating cells when non-differentiated can correct hereditary disorders such as beta-thalassemia and sickle cell anemia. It is known that the surface concentration of proteoglycans non-differentiated cells is very low. When these cells begin to differentiate, proteoglycan expression on the cell surface is increased. By understanding the reasons why the transfection efficiency of these cells is typically low, it may be possible to alter the transfection conditions to transfect these cells successfully.

It is therefore an object of the present invention to provide methods for increasing the efficiency of transfection, whether performed in vitro, in vivo, or ex vivo.

It is a further object of the present invention to provide methods for decreasing the efficiency of transfection.

It is still a further object of the present invention to provide a method for improving the transfection efficiency for non-differentiated cells.

SUMMARY OF THE INVENTION

The present invention provides methods for controlling transfection mediated by complexes of genetic material with a cationic species, and, in particular, cationic liposomes. Transfection mediated by these complexes is known in the art. This method of transfection is described with respect to complexes including cationic liposomes, for example, in PCT WO 93/14778 to Vical, Inc., the contents of which are hereby incorporated by reference.

The genetic material is preferably used herein as a complex with a cationic species. The size of poly-L-lysine-DNA complexes and complexes of genetic material and cationic liposomes used for transfection is typically between approximately 10 and 300 nm. Preferably, complexes for use in the present methods have a size between approximately 10 and 300 nm, and, more preferably, between 20 and 150 nm.

The mechanism by which the complex interacts with the cell to be transfected has been the subject of debate. Applicant has demonstrated that the cationic species interact with the polyanionic proteoglycans present on the surface of cells that are to be transfected. Applicant's data show a direct correlation between transfection efficiency and proteoglycan expression on the cell surface.

Transfection efficiency can be lowered by lowering the proteoglycan expression on the cell surface, and can be increased by increasing the proteoglycan expression on the cell surface. Various compounds are known to increase the amount of proteoglycans on the cell surface. These compounds include, but are not limited to, phorbol esters such as 12-O-tetradecanoylphorbol-13-acetate (TPA) and phorbol-12-O-myristoyl-13-acetate (PMA), EGF, IGF-1, IL-3, IL-5, FGF, Interferon, PDGF, and TGF beta. Preferred compounds for increasing the amount of proteoglycans on the cell surface are phorbol esters. More preferably, the phorbol esters are TPA or PMA.

When transfection is performed in vitro, cells to be transfected are contacted with an effective amount of a complex of a cationic substance and genetic material to effectively transfect all or a portion of the cells, and an effective amount of a material known to increase the expression of proteoglycans on the cell surface.

Genetic material can also be delivered to a cell ex vivo. In this embodiment, live cells are first removed from the organism to be transfected. Then, the cells are contacted with a preparation that includes an effective amount of a complex of a desired genetic material and a cationic substance, preferably a cationic lipid, to deliver the genetic material into the cells, in combination with an effective amount of a substance known to increase proteoglycan expression on the cell surface. After transfection, the cells are returned to the organism. In addition to complexing the genetic material with the cationic species, the amount of proteoglycans on the cell surface is increased to increase the binding of the complex with the cell surface. In this fashion, the efficiency of transfection is increased.

Optionally, ex vivo transfection can include a selection step to separate or expand the transfected cells. Preferably, when the cells are removed from the organism, the cells are substantially separated from the surrounding extracellular matrix.

When genetic material is transfected for the purpose of expressing a protein, the expression may be transient, or may persist for a substantial length of time. In one embodiment, the genetic material encodes a polypeptide that is adapted to treat a disease caused by a functional gene deficiency. In another embodiment, the polypeptide is an immunogenic polypeptide in the organism. In such a case, the organism, which is preferably a mammal, and, more preferably a human, develops an immune response against the immunogen after the transfected cells are returned. This method may be used to immunize the organism. In one embodiment, the genetic material operatively codes for lymphokine. Cells that may be transfected include, but are not limited to, white blood cells, myoblasts, and bone marrow cells.

When transfection is performed in vivo, glycosaminoglycans and other polyanionic species in the plasma can adversely affect the transfection efficiency. Transfection efficiency can be increased by lowering the plasma concentration of glycosaminoglycans and, optionally, other polyanionic species, and can be decreased by increasing the plasma concentrations of glycosaminoglycans. Various compounds are known to lower the plasma concentration of glycosaminoglycans. These compounds include, but are not limited to, protease inhibitors, plasma lipoproteins, growth factors, lipolytic enzymes, extracellular matrix proteins, and platelet factor 4. Preferred compounds for minimizing the plasma concentration of glycosaminoglycans are protease inhibitors and plasma lipoproteins. More preferably, the compounds are protease inhibitors.

When the transfection is performed in vivo, the complex is administered with an effective amount of a substance that increases the expression of proteoglycans on the cell surface, and optionally with an effective amount of a compound that decreases the plasma concentration of glycosaminoglycans. The complex and the compounds can be administered at the same time or within a reasonable time of each other, so long as the overall effect is that the cell surface concentration of proteoglycans increases and, optionally, the plasma concentration of glycosaminoglycans decreases, when transfection occurs.

The mode of administration can be any mode that effectively targets the complex to the desired cells. Suitable modes of administration for use in the present invention include, but are not limited to, oral, parenteral, intravenous, intramuscular, intrauteral, intraperitoneal, and intranasal. For example, lung tissue can be targeted by administering the complex intranasally via an aerosol.

When the cationic species is a cationic liposome, the liposome can be prepared to specifically target a certain cell type. For example, certain antibodies are known to target liposomes to various cells. Tumor cells or ischemic tissue can be targeted by using unilamellar vesicles less than 200 nm in diameter.

Understanding the role of proteoglycans in transfection also allows for the selective or non-selective reduction of transfection efficiency. Non-selectively minimizing transfection efficiency can be important in preventing or minimizing viral infections, in cases where viruses bind and enter cells through polyanionic sites on the cell surface, rather than to other cell receptors. To minimize viral infection, the amount of proteoglycans on the cell surface can be reduced, and/or the concentration of glycosaminoglycans or other polyanionic substances in the plasma can be increased. The amount of proteoglycans on the cell surface can be minimized by adding various compounds that are known to lower cell surface concentration of proteoglycans. Examples of these compounds include, but are not limited to, xylosides and catabolic cytokines such as GM-CSF, IL-1 alpha and beta, and TNF-alpha. Preferred compounds for minimizing the amount of proteoglycans on the cell surface are xylosides and catabolic cytokines such as IL-1 alpha and beta, and TNF-alpha.

The plasma concentration of glycosaminoglycans can be lowered by adding an effective amount of a compound that decreases the plasma concentration of glycosaminoglycans. Examples of these compounds include, but are not limited to, protease inhibitors, plasma lipoproteins, growth factors, lipolytic enzymes, extracellular matrix proteins, and platelet factor 4.

Plasma concentration of glycosaminoglycans and other polyanions can be increased by either direct administration of glycosaminoglycans or other polyanions, or by administration of compounds known to increase the plasma concentration of these species.

Methods for selectively reducing transfection efficiency can be used to target cells in which transfection is not desired, by lowering the proteoglycan expression on the surface of those cells, and then introducing genetic material to cells in which transfection is desired. In this embodiment, an effective amount of a compound that minimizes proteoglycan expression on the cell surface is administered to the cells in which transfection is not desired. The administration to these cells can be by any suitable mode that localizes these compounds in the desired cells. Suitable modes for administering these compounds include those described above for in vivo transfection.

Transfection efficiency can also be controlled by modifying proteoglycan expression such that the cells express the various proteoglycans on the cell surface in a different ratio than untreated cells. In some cases, higher concentrations of chondroitan-based proteoglycans on the surface of cells causes increased transfection efficiency, whereas in others, higher concentrations of heparan sulfate-based proteoglycans on the surface of cells causes increased transfection efficiency. One of skill in the art can readily determine which proteoglycans are preferred. Methods for modulating the ratio of heparan sulfate to chondroitin sulfate using glycosaminoglycan biosynthesis inhibitors is known in the art, as described in Timar, et al., *Int. J Cancer*, 62:755–761 (1995). Suitable glycosaminoglycan biosynthesis inhibitors for use in the present invention include, but are not limited to, β-D-xyloside, 2-deoxy-D-glucose, ethane-1-hydroxy-1, 1-diphosphonate and 5-hexyl-2-deoxyuridine.

Transfection efficiency can be increased by complexing genetic material with a cationic lipid that is covalently or ionically bound to an agent known to increase the amount of proteoglycans on the cell surface. Alternatively, neutral lipids, lysolipids and neutral phospholipids can be covalently or ionically bound to an agent known to increase the amount of proteoglycans on the cell surface, and these modified lipids can be included in a cationic liposome formulation. Cationic liposomes prepared from the resulting lipids also increase transfection efficiency by increasing the concentration of cell surface proteoglycans.

For example, phorbol esters such as TPA and PMA can be reacted with a suitable lipid with one or more hydroxy or amine groups to form an ester or amide linkage. Anabolic cytokines with reactive functional groups can be similarly coupled to suitable lipids using known chemistry.

Alternatively, lipids covalently or ionically linked with substances known to decrease the cell surface expression of proteoglycans can be administered to those cells in which transfection is not desired, before a complex of genetic material and a cationic species is administered to cells in which transfection is desired. For example, xylosides or catabolic cytokines with reactive functional groups can be covalently linked to suitably functionalized lipids to prepare modified lipids that reduce the cell surface expression of proteoglycans. Cytokines, whether anabolic, catabolic or modulatory, can be covalently linked to these lipids to form compounds that increase, decrease or otherwise modulate expression of proteoglycans on the cell surface.

In another embodiment, the complex is co-administered with a therapeutic agent. Suitable therapeutic agents for use in practicing the present invention include, but are not limited to, cytotoxic agents, antifungal agents, antibacterial agents, antiviral agents, immunomodulating agents, anti-inflammatory agents, vasoconstrictors, and vasodilators.

In another embodiment, the efficiency of transfection of non-differentiated cells can be increased by causing the non-differentiated cells to express proteoglycans at or near the time the cells are transfected.

DETAILED DESCRIPTION OF THE INVENTION

Definitions

Figure 1:
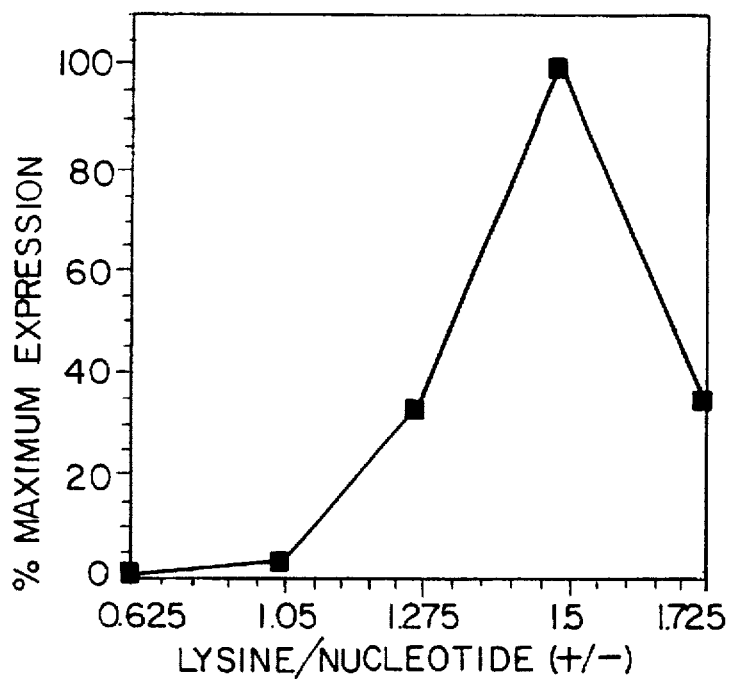
FIG. 1 is a graph of the effect of net complex charge on expression of DNA, showing the percent of maximum expression versus the ratio by charge of lysine to nucleotide.

Transfection is defined herein as the intracellular delivery of genetic material, for example, DNA and mRNA, into the cells of an organism, preferably a mammal, and more preferably, a human. In one embodiment, the genetic material is expressible, and produces beneficial or interesting proteins after being introduced into the cell. In other embodiments, the genetic material is used to bind to or interact with a site within the cell, or encodes a material that binds to or interacts with a site within the cell. In embodiments wherein a virus binds to and enters cells via polyanionic sites on the cell surface, the methods for increasing or decreasing transfection efficiency also have an effect on viral infection.

The terms "polypeptide" and "protein" are used interchangeably. Suitable cell types that can be transfected using the methods described herein include, but are not limited to, fibroblasts, myoblasts, hepatocytes, cells of hematopoetic origin such as white blood cells and bone marrow cells, cancer cells and ischemic tissue. Transfection can be performed in vitro, ex vivo, or in vivo. The genetic material can be transiently expressed or stably expressed.

In vitro transfection involves transfecting cells outside of the living organism, for example, using cell cultures. In vivo transfection involves transfecting cells within a living organism. Ex vivo transfection involves removing cells from an organism, transfecting all or a portion of the cells, and returning the cells to the organism.

The term "removing" is used to describe any method known to those with skill in the art to obtain a sample of live cells from an organism. Methods to remove a live cell sample include, but are not limited to, venipucture, cell scraping, and biopsy techniques that include punch biopsy, needle biopsy and surgical excision. The term "returning" includes methods known to those with skill in the art to replace cells in the body. These include, but are not limited to, intravenous introduction, surgical implantation and injection.

Transient gene expression is generally defined as temporary gene expression that diminishes over time under selective conditions. Transient expression can more broadly be defined as gene expression occurring over periods of less than one year to periods as short as one week or one month. The gene therapy application, the vector construct, whether or not chromosome integration has occurred, the cell type and the location of cell implantation following transfection will all influence the length of time that a particular gene is expressed. Transient expression is often desirable in the practice of the present invention to permit use of the transiently transfected cells as a drug. In this embodiment, a gene can be administered periodically, the dosage can be adjusted, and the effect is ultimately transient.

Stable gene expression is generally defined as gene expression that does not significantly diminish over time, wherein the transfected cells manufacture a relatively constant level of gene product for relatively long periods of time.

Genetic material is defined herein as DNA, RNA, mRNA, ribozymes, antisense oligonucleotides, modified polynucleotides and oligonucleotides, including SELEX oligomers, protein nucleic acid (PNA) or a combination thereof. Modified polynucleotides and oligonucleotides are defined as those polynucleotides and oligonucleotides that contain non-naturally occurring nucleotides. Modified nucleosides can be incorporated into the genetic material to impart in vivo and in vitro stability of the oligonucleotides to endo and exonucleases, alter the charge, hydrophilicity or lipophilicity of the molecule, and/or provide differences in three dimensional structure.

Nucleoside modifications that have been previously described include 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, and methylations. Modifications have also included 3' and 5' modifications such as capping.

PCT WO 91/14696, incorporated herein by reference, describes a method for chemically modifying antisense oligonucleotides to enhance entry into a cell.

The genetic material is preferably used herein as a complex with a cationic species. The size of poly-L-lysine-DNA complexes and complexes of genetic material and cationic liposomes typically used for transfection is typically between approximately 10 and 300 nm. Preferably, complexes for use in the present methods have a size between approximately 10 and 300 nm, and, more preferably, between approximately 20 and 150 nm.

Cationic species suitable for use in the present invention include, but are not limited to, cationic lipids, cationic liposomes, cationic polyamino acids such as poly-L-lysine, polybrene, and polyornithine, lipopolyamine, polyethylene imine, DEAE-dextran, cationic amphiphiles, calcium ions, and dendrite polymers containing cationic functional groups. Preferably, the cationic species is a cationic lipid or a cationic liposome.

Cationic liposomes are liposomes that contain lipid components that have an overall positive charge at physiological pH.

Cationic amphiphilies are species that contain both a lipid component and a polycationic component. Examples of these include cationic polyamino acids, for example poly-L-lysine, that contain lipid sidechains.

Suitable cationic lipids for use in the present invention include, but are not limited to, DOTMA, Lipofectin (GIBCO/BRL, Gaithersburg, Md.), 1,2-bis(oleoyloxy)3-(trimethylammonio)propane (DOTAP), N-(w, w-1-dialkoxy)-alkyl-N,N,N-trisubstituted ammonium surfactants, complex cationic lipids having similar structures and properties and mixtures of these. Particularly preferred cationic lipids are those cationic lipids that are readily degradable in vivo. These include analogs of DORI (DL-1, 2-dioleoyl-3-dimethylaminopropyl-$\beta$-hydroxyethylammonium) and DORIE (DL-1,2-O-dioleyl-3-dimethylaminopropyl-$\beta$-hydroxyethylammonium) as well as DORI ester/ether compounds (DL-1-O-oleyl-2-oleoyl-3-dimethylaminopropyl-$\beta$-hydroxyethylammonium or DL-1-oleoyl-2-O oleyl-3-dimethyl-aminopropyl-$\beta$-hydroxyethylammonium).

Other neutral lipids may be added to the desired cationic lipid or mixture of lipids. These lipids include, but are not limited to, lyso lipids, such as lysophosphatidylcholine (I-oleoyllysophosphatidylcholine), cholesterol, or neutral phospholipids such as dioleyl phosphatidyl ethanolamine (DOPE), dioleoyl phosphatidyl choline (DOPC), dimyristoyl phosphatidyl choline (DMPC), and dipalmitoyl phosphatidyl choline (DPPC). The ratios of lipids may vary to include a majority of cationic lipid in combination with cholesterol and/or mixtures of lyso or neutral lipids.

The ratio by charge of cationic lipid to genetic material is between approximately 1.5 and 6. The optimum ratio varies with the type of cationic species. However, optimization is routine in the art.

A glycosaminoglycan (GAG) is a linear heteropolysaccharide possessing a characteristic disaccharide repeat sequence. One monosaccharide of the disaccharide repeat is an amino sugar with D-glucosamine or galactosamine, and the other unit is typically, but not always, a uronic acid residue of either D-glucuronic acid or iduronic acid. Both units are variably N- and O-sulfated, which adds to the heterogeneity of these complex macromolecules The most common GAG structures are chondroitin sulfate, dermatan sulfate, keratan sulfate, hyaluronic acid, heparin and heparan sulfate.

Various compounds are known to lower the plasma concentration of glycosaminoglycans. These compounds include, but are not limited to, protease inhibitors, plasma lipoproteins, growth factors, lipolytic enzymes, extracellular matrix proteins, and platelet factor 4. Preferred compounds for minimizing the plasma concentration of glycosaminoglycans are protease inhibitors and plasma lipoproteins. More preferably, the compounds are protease inhibitors.

Various compounds are known to increase the plasma concentration of glycosaminoglycans.

A proteoglycan (PG) is formed when a glycosaminoglycan is covalently attached at the reducing end through an O-glycosidic linkage to a serine residue or N-linked to asparagine in a core protein. A major function of cell surface proteoglycans is in cell adhesion and migration. These processes are generally thought to be mediated by interactions between the proteoglycans and extracellular matrix components such as laminin, collagen, and fibronectin. The negative charge of the proteoglycans is similar to the negative charge of the glycosaminoglycans, and is largely due to the sulfation of the glycosaminoglycan moiety in the proteoglycan.

Various compounds are known to increase the amount of proteoglycans on the cell surface. These compounds include, but are not limited to, phorbol esters such as TPA and PMA, and cytokines such as EGF, IGF-1, IL-3, IL-5, FGF, Interferon, PDGF, and TGF beta. Preferred compounds for increasing the amount of proteoglycans on the cell surface are phorbol esters. More preferably, the phorbol esters are TPA or PMA.

Various compounds are known to decrease the amount of proteoglycans on the cell surface. These compounds include, but are not limited to, xylosides, GM-CSF, IL-1 alpha and beta, and TNF-alpha. Preferred compounds for decreasing the amount of proteoglycans on the cell surface are xylosides, IL-1 alpha and beta, and TNF-alpha.

Cytokines are polypeptide mediators which can be produced by a variety of cells. Cytokines such as interleukin 3 mediate proteoglycan expression on the surface of cells (Nietfeld, Experientia 49:456–469 (1993). Suitable cytokines for use in practicing the present invention include, but are not limited to, epidermal growth factor (EGF), fibroblast growth factor (FGF), granulocyte colony stimulating factor (GCSF), granulocyte macrophage colony stimulating factor (GMC-SF), interferon gamma (IG), insulin-like growth factor-1 (ILGF), interleukin-1 alpha (IL-1 alpha), interleukin-1 beta (IL-1 beta), interleukin-1 receptor antagonist (IL-1 RA), interleukin-3 (IL-3), interleukin-4 (IL-4), interleukin-5 (IL-5), interleukin-6 (IL-6), macrophage colony stimulating factor (MCSF), platelet derived growth factor (PDGF), transforming growth factor beta (TGF beta), and tumor necrosis factor alpha (TNF alpha).

Generally, certain cytokines are anabolic, certain are both anabolic and modulatory, certain are catabolic, and certain are both catabolic and modulatory. Catabolic cytokines inhibit proteoglycan synthesis and/or promote proteoglycan degradation. Catabolic cytokines include IL-1 alpha and beta, and TNF-alpha. Anabolic cytokines stimulate proteoglycan synthesis and/or inhibit proteoglycan degradation. Anabolic cytokines include EGF, IGF-1, IL-3, and IL-5. Modulatory cytokines regulate the effects of the anabolic and catabolic cytokines. Modulatory cytokines include G-CSF, IL-4, and M-CSF.

Further, many cytokines are multifunctional, and may elicit more than one effect in a target cell. However, one of skill in the art can readily determine the effect elicited from administration of a particular cytokine on a particular cell type, by determining whether proteoglycan expression on the cell surface has been increased or decreased. Cytokines that are both anabolic and modulatory include FGF, Interferon, PDGF, and TGF beta. Cytokines that are both catabolic and modulatory include GM-CSF. IL-6 has all three properties.

The present invention provides methods for controlling transfection that is mediated by complexes of genetic material with cationic species such as cationic liposomes. Transfection mediated by these complexes is known in the art. This method of transfection is described with respect to complexes including cationic liposomes, for example, in PCT WO 93/14778 to Vical, Inc., the contents of which are hereby incorporated by reference. Briefly, transfection efficiency is increased by increasing the cell surface expression of proteoglycans, and is decreased by decreasing the cell surface expression of proteoglycans. In the presence of plasma, transfection efficiency is also increased by decreasing the plasma concentration of glycosaminoglycans, and is decreased by increasing the plasma concentration of glycosaminoglycans, to the extent that effecting the concentration of glycosaminoglycans in the plasma can occur without significant effect on the cell surface concentration of proteoglycans.

This invention has a number of applications, some of which will be discussed in detail below. The methods can be used to express exogenous polynucleotide in a variety of tissues. For example, liver cells can be transfected with the LDL receptor to reduce serum cholesterol in vivo, and muscle can be removed to treat the cells with the defective gene product involved in Duchennes muscular dystrophy. Progenitor cells from the hematopoietic system can be treated at a predifferentiated stage to correct hereditary disorders such as beta-thalassemia. The method is contemplated to be particularly useful for the treatment of diseases caused by a functional gene deficiency. For these applications, the polynucleotide encoding exogenous polypeptide codes for the polypeptide deficient or malfunctioning in that particular genetic disease.

Transient expression of a gene product can be advantageously used to promote an immune response. Thus, viral diseases can be treated by interferon expression and cytokines can be used to stimulate the immune system to react against foreign antigens or cancers. Similarly, foreign proteins can be expressed transiently from target cells to generate an immune response.

The mechanism by which the cationic species interacts with the cell to be transfected has been the subject of debate. The present inventor has determined that the cationic species interact with the polyanionic proteoglycans present on the surface of cells that are to be transfected. Applicant's data show a direct correlation between transfection efficiency and proteoglycan expression on the cell surface.

Transfection efficiency can be lowered by lowering the proteoglycan expression on the cell surface, and can be increased by increasing the proteoglycan expression on the cell surface.

Complexes of DNA and cationic species are often used to increase the efficiency of transfection relative to using naked DNA. Transfection using these complexes, for example, complexes of DNA with cationic liposomes, has been extensively described.

Polyanionic glycosaminoglycans are present in blood plasma, and also interact with the complex. This interaction is one of the factors responsible for the non-reproducibility of transfection conditions used in vitro or ex vivo when the same conditions were attempted in vivo.

Evaluation of the Effect of Proteoglycans on Transfection Efficiency

Transfection has been mediated by complexing DNA with poly-L-lysine (PLL:DNA). There are large differences between polylysine mediated transfection in HeLa (adherent) cells and K562 (suspension) cells. Various cellular sites, in particular, sites with polyanionic compounds such as membrane-associated proteoglycans, interact with polylysine-DNA complexes. Applicant has determined that membrane-associated proteoglycans mediate the delivery of polylysine-DNA complexes into cells.

A variety of assays were employed to determine that membrane-associated proteoglycans mediate transfection. In the assays, transfection efficiency was measured by determining lucerifase expression of the transfected gene. Since ionic interactions between proteoglycans and cationic substrates often depend on the sulfation of glycosaminoglycan chains, transfection was assayed in HeLa cells cultured in the presence of sodium chlorate, an inhibitor of glycosaminoglycan sulfation, as shown in Example 2. Transfection was also tested in cells pre-treated with glycosaminoglycan lyases and exogenous glycosaminoglycans, as shown in Example 3. In addition, the transfection efficiency of polylysine-DNA in wild-type Chinese Hamster Ovary (CHO) cells was compared to that of mutant CHO cells unable to synthesize proteoglycans, as shown in Example 5.

The ratio of gene delivery agent to DNA is an important variable affecting transfection efficiency. Many laboratories have reported that on the basis of charge, gene delivery agents must be added in excess over oligonucleotide to obtain maximum expression. To determine the optimum charge ratio in the polylysine system, complexes prepared with 1.5 mg DNA and varying amounts of polylysine were transfected into HeLa cells. As shown in FIG. 1, complexes composed of a small lysine/oligonucleotide ratio yielded very little expression. However, expression increased dramatically as complexes became more cationic. Maximum luciferase expression was $5 \times 10^5$ relative light units (RLU) $/10^6$ cells at a lysine/oligonucleotide charge ratio of approximately 1.5. Complexes of the optimum composition were used for all subsequent experiments. These results are consistent with an ionic model to describe cell-DNA complex interactions that anionic membrane residues likely participate in the transfection of complexes of cationic species with genetic material, for example poly-L-lysine (PLL):DNA.

Sulfates Mediate PLL-DNA Transfection

The interactions of proteoglycans with biological molecules are largely ionic and depend on the sulfation of the glycosaminoglycan chains. In fact, the involvement of proteoglycans in cellular processes is often demonstrated by treating cells with sodium chlorate, a potent inhibitor of glycosaminoglycan sulfation. Chlorate competitively inhibits ATP-sulfuryltransferase, an enzyme essential in the synthesis of PAPS, a co-substrate of protein sulfation.

Figure 2A:
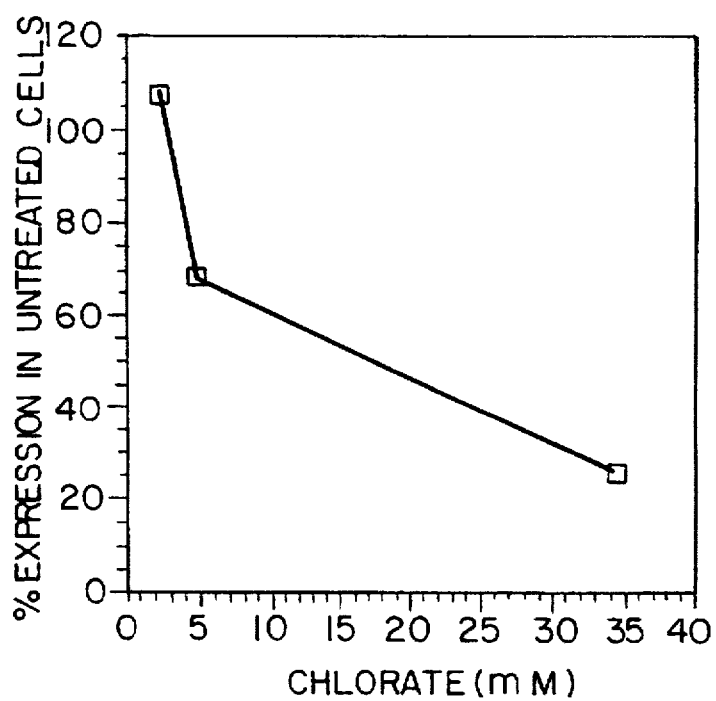
FIG. 2A is a graph of the effect of the concentration of chlorate ion on luciferase expression, showing the percent of expression in untreated cells versus the millimolar concentration of chlorate ion.

To test the role of sulfated proteoglycans in transfection, cells were incubated in different concentrations of sodium chlorate for 48 hours and transfected with PLL-DNA, using the protocol shown below in Example 2. Expression was inhibited by chlorate in a concentration dependent manner (FIG. 2A). At 35 mM chlorate, a 70% reduction in luciferase expression was observed. Cellular morphology and proliferation remained normal at all concentrations.

Figure 2B:
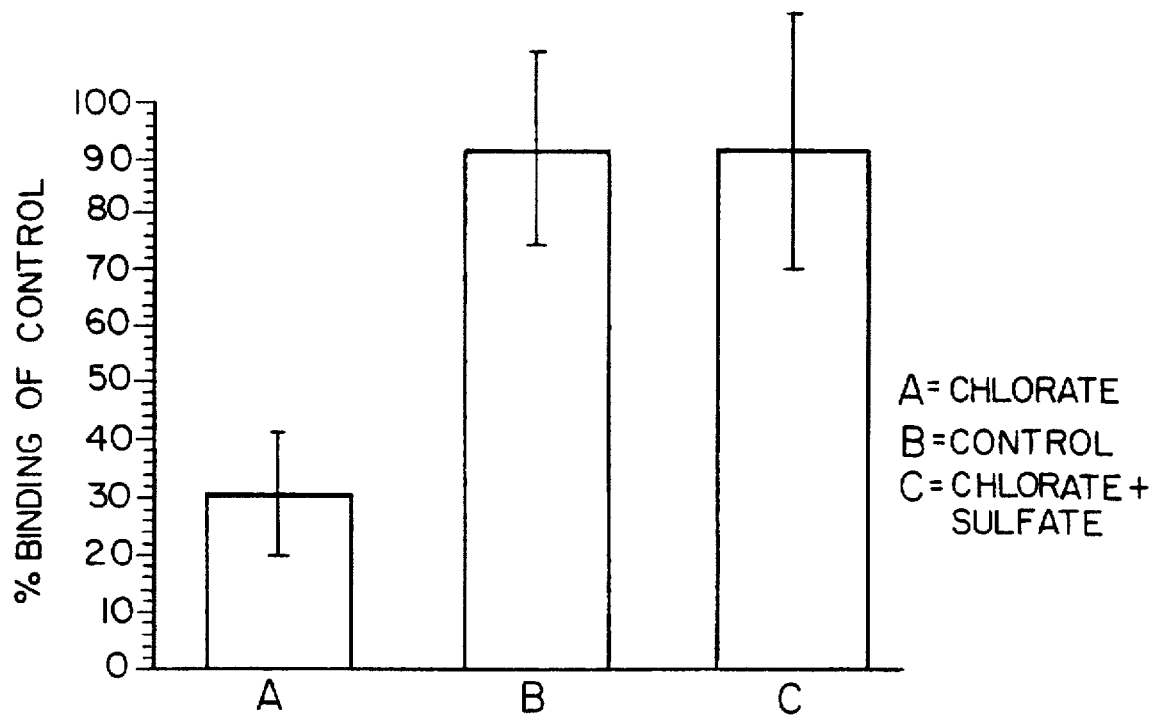
FIG. 2B is a bar graph of the effect of the chlorate ion treatment on the binding of PLL-DNA to HeLa cells. The percent binding of control is shown for chlorate ions, a control group without chlorate ions, and a combination of chlorate and sulfate ions.

To determine whether these results were merely artifacts unrelated to the mechanism of transfection, Applicant evaluated whether the effects of chlorate on expression were due to an inhibition of DNA uptake. DNA was labeled with YOYO, a fluorescent intercalator, complexed with polylysine and incubated with chlorate treated (35 mM) and untreated HeLa cells. After 4 hours, cells were washed, fixed, and imaged by confocal microscopy to localize intracellular fluorescence. As shown in FIG. 2B uptake of PLL-YYDNA was severely impaired in chlorate treated cells.

Additional experiments were conducted to determine whether chlorate treatment inhibited binding of PLL-DNA to the cell's surface. Complexes of polylysine and nick translated plasmid were prepared and incubated with chlorate treated and untreated HeLa cells for four hours at 4° C. to inhibit endocytosis. Cells were washed extensively with ice cold phosphorus buffered saline (PBS), dissolved, and assayed for cell associated radioactivity. It was observed that binding of PLL-DNA to chlorate treated cells was inhibited 69 ($\pm 14$)% with respect to untreated cells. HeLa cells co-treated with chlorate and excess sulfate bound as much PLL-DNA as untreated cells. Furthermore, cells exposed to chlorate for only four hours experienced no inhibitory effect on expression or uptake. Therefore, the effects of chlorate on binding, uptake and expression are likely due to desulfation of membrane bound molecules participating in transfection. These results suggest that sulfated proteoglycans are involved with binding and internalizing PLL-DNA.

Figure 3A:
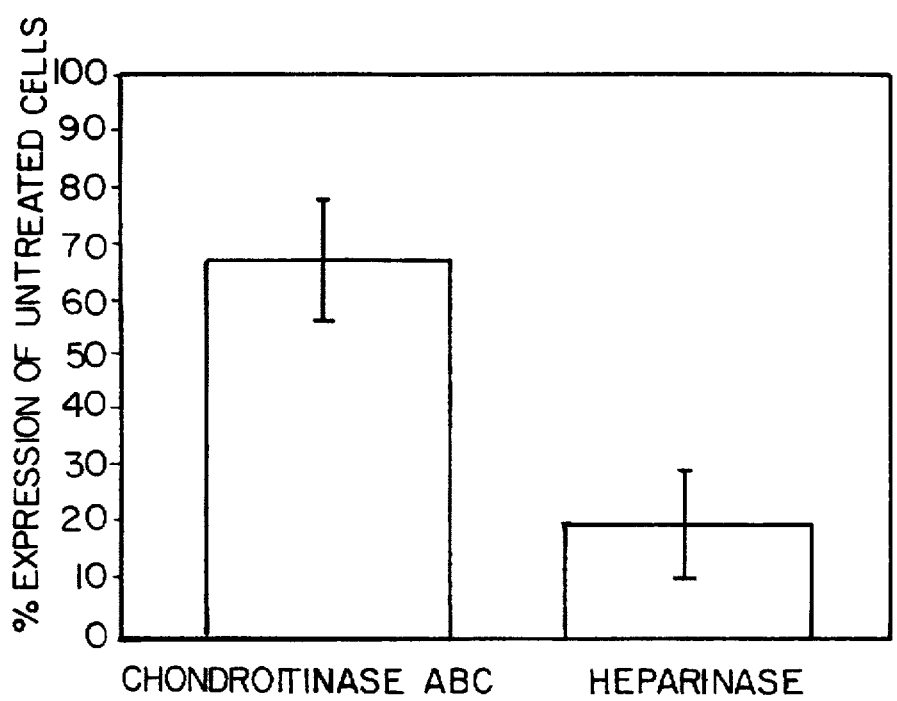
FIG. 3A is a bar graph of the effect of lyases on expression. The percent expression of untreated cells is shown for a group treated with chondroitinase ABC and for a group treated with heparinase.

Effect of Exogenous Glycosaminoglycans and Glycosaminoglycan Lyases on Transfection of PLL-DNA Experiments were conducted to test the involvement of specific proteoglycans in transfection. Cells were incubated with glycosaminoglycan lyases for 1.5 hours, rinsed, and transfected as per the normal protocol, as described below in Example 4. Heparinase II, active on both heparin and heparan sulfate glycosaminoglycans, had the most profound effect on transfection, reducing expression by 78%, as shown in FIG. 3A. Chondroitinase ABC, targeting all three chondroitan sulfates, reduced expression by 20%. Hyaluronase, active on non-sulfated hyaluronic acid only, did not reduce luciferase expression by any measurable extent.

Figure 3B:
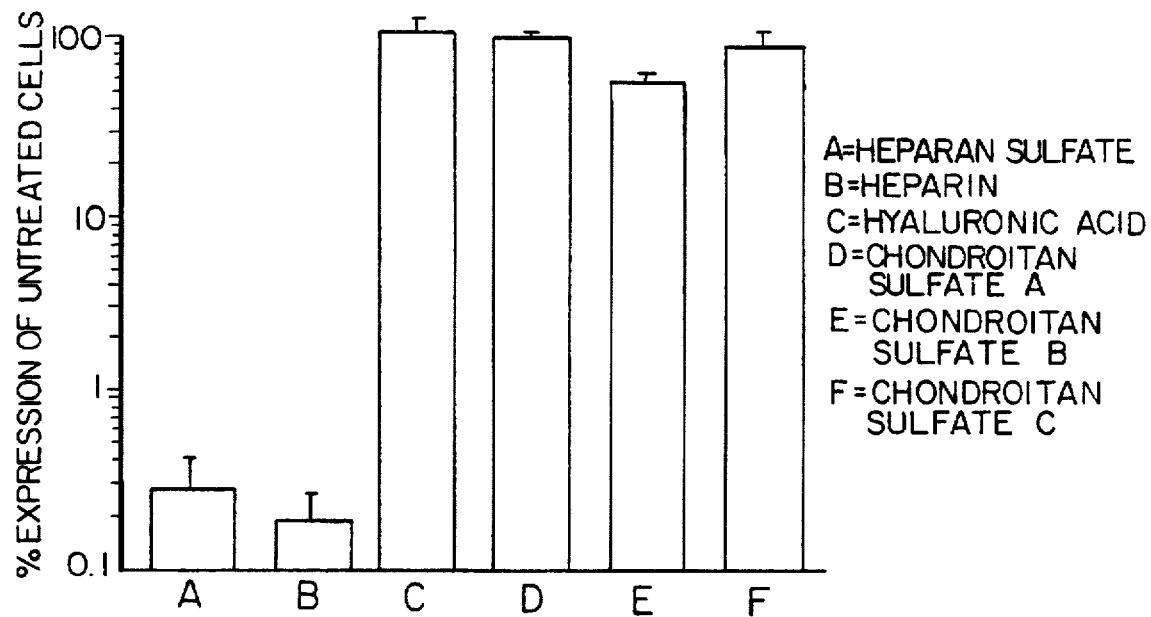
FIG. 3B is a bar graph of the effect of exogenous glycosaminoglycans on expression. The percent expression of untreated cells is shown for groups treated with heparan sulfate, heparin, hyaluronic acid, chondroitin sulfate A, chondroitin sulfate B, and chondroitin sulfate C.

To test whether exogenous glycosaminoglycans could competitively inhibit transfection, HeLa cells were transfected in the presence of free glycosaminoglycans (40 mg/ml) in the transfection media. In accordance with glycosaminoglycan lyase experiments, heparin and heparan sulfate competitively inhibited luciferase expression while, at this concentration, chondroitans A and C and hyaluronic acid did not (FIG. 3B). Chondroitan sulfate B, the third most sulfated glycosaminoglycan, reduced expression by 40%.

Figure 3C:
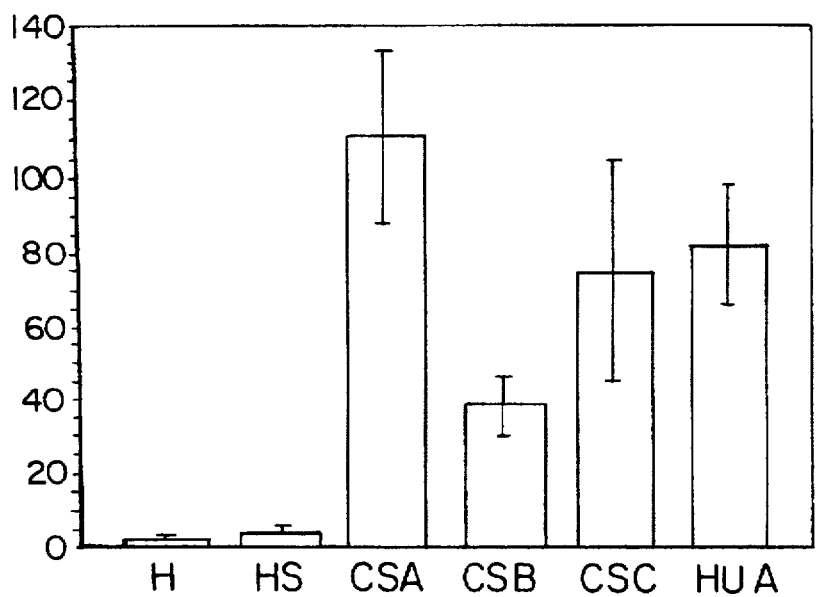
FIG. 3C is a bar graph of the effect of glycosaminoglycans on binding. The percent binding of untreated cells is shown for groups treated with heparan sulfate (HS), heparin (H), hyaluronic acid (HUA), chondroitin sulfate A (CSA), chondroitin sulfate B (CSB), and chondroitin sulfate C (CSC).

Experiments were conducted to determine whether the endocytosis of DNA was affected by exogenous glycosaminoglycans. PLL-YYDNA complexes and glycosaminoglycans were incubated with HeLa cells for four hours at 37° C. Cells were rinsed, fixed and mounted onto glass slides. Confocal microscopy images of intracellular fluorescence (FIG. 3C) revealed a correlation between expression and DNA uptake in the presence of competing glycosaminoglycans. Heparin and Heparan sulfate drastically hampered both expression and uptake of DNA. Chondroitan sulfates A and C did not inhibit expression or endocytosis of DNA. Chondroitan sulfate B moderately reduced uptake of PLL-YYDNA, which would explain the modest decrease in expression as well. These results suggest that heparin, heparan sulfate, and chondroitan sulfate B bind to complexes of cationic species and genetic material, for example, PLL-DNA.

Cells Lacking Proteoglycans Are Transfection Deficient

Chinese Hamster Ovary (CHO) cells are highly susceptible to polylysine mediated transfection. To demonstrate that transfection depends on the level of proteoglycan expression in these cells, transfection was performed in CHO-pgs745 cells, a mutant deficient in xylosyltransferase, an initiator of proteoglycan synthesis. Despite an inability to produce proteoglycans, CHO-pgs745 cells are highly proliferative and are morphologically indistinct from their wild-type counterparts.

Figure 4A:
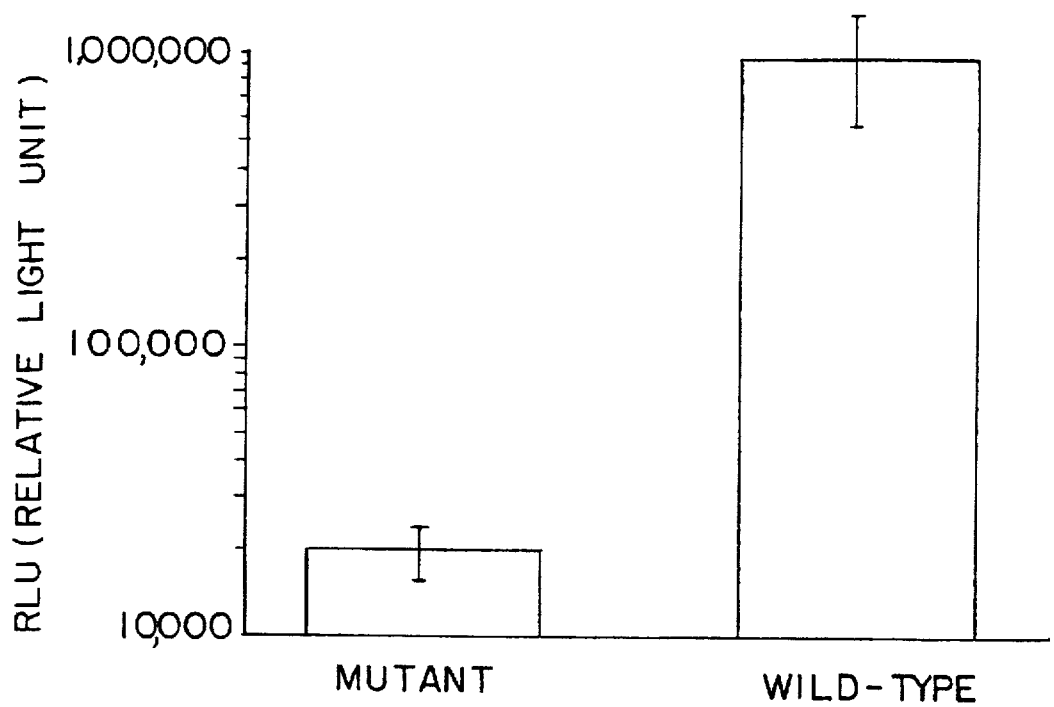
FIG. 4A is a bar graph showing luciferase expression in wild-type and mutant Chinese hamster ovary (CHO) cells.
Figure 4B:
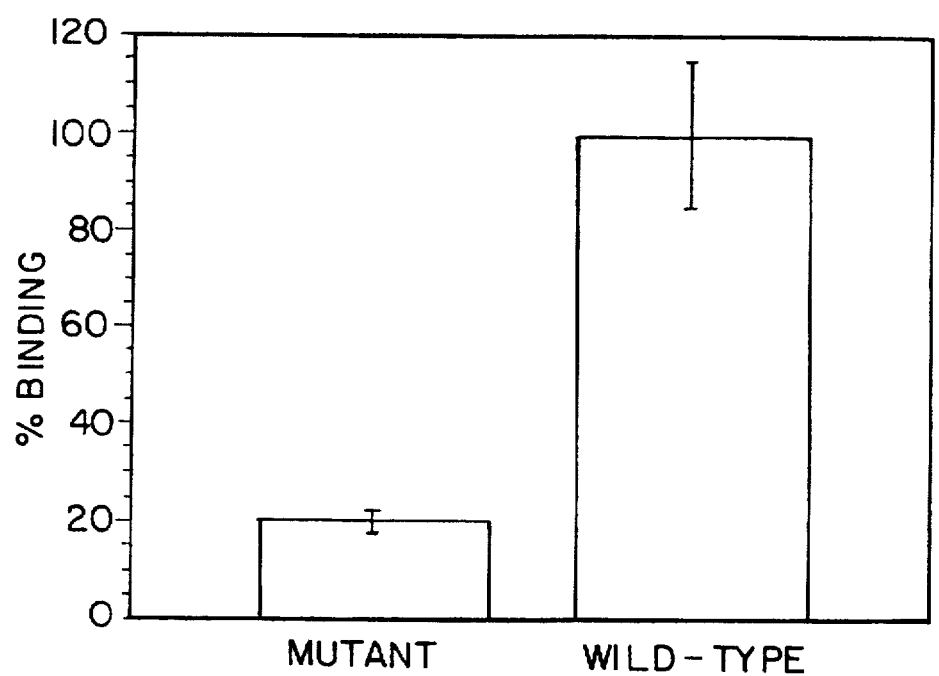
FIG. 4B is a bar graph of the effect of proteoglycan expression on the binding of wild-type and mutant CHO cells.

Both CHO-K1 and CHO pgs-745 cells were transfected as described below in Example 4. As shown in FIG. 4A, luciferase expression was nearly 60 times lower in the proteoglycan deficient cells. In addition, the uptake of PLL-YYDNA into CHO-pgs745 cells was dramatically lower than in the wild-type cultures. As shown in FIG. 4B, cellular binding of radiolabeled complexes at 4° C. was similarly impaired. Therefore, cells unable to express proteoglycans are transfection incompetent.

Evaluation of the Role of Proteoglycans on Transfection with Cationic Lipid:DNA Complexes Since polylysine is not a widely used transfection agent, experiments were conducted to evaluate the role of proteoglycans on transfection with cationic lipid:DNA complexes. The cationic lipids used were obtained from a PerFect Transfection Kit (Invitrogen). The exact structures of the lipids in the kit are proprietary information. Luceriferase expression in wild-type cultures relative to proteoglycan deficient cells varied depending on the lipid.

Figure 5A:
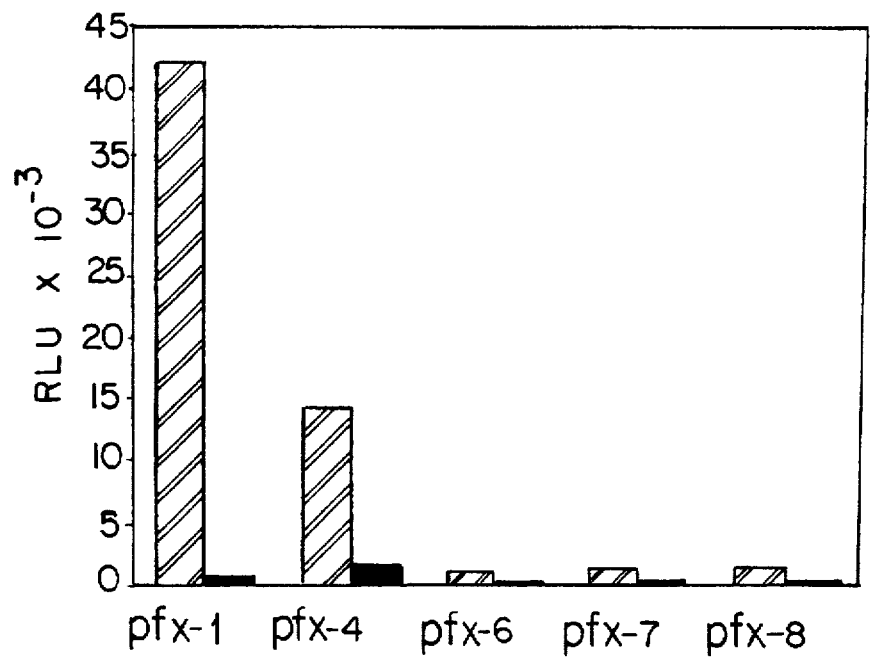
FIG. 5A is a bar graph showing the luciferase expression in relative light units (RLU) for cationic lipid-mediated transfection in wild-type and mutant Chinese hamster ovary (CHO) cells. The solid lines represent expression in mutant cells, and the dashed lines represent expression in wild-type cells.
Figure 5B:
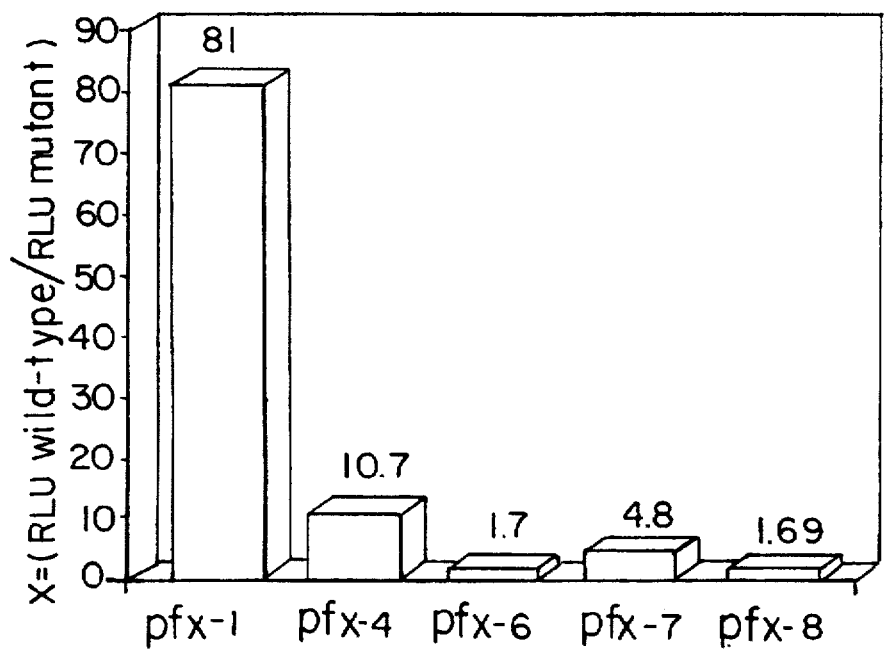
FIG. 5B is a bar graph showing the dependence of the correlation factor X (the ratio of the luciferase expression in wild-type and mutant Chinese hamster ovary (CHO) cells) on the cationic lipids used for transfection.

The strongest correlation between transfection and proteoglycans and the highest expression levels were obtained by pfx-1 and pfx-4 lipids which consist of a mixture of two cationic lipids. The weakest correlation and the lowest expression levels were obtained with lipid formulations consisting of a 1:1 mixture of a cationic lipid and DOPE or a single cationic lipid. Wild-type and mutant cells (approximately $2 \times 10^5$ cells/well) were transfected with approximately 0.2 µg DNA and the optimum amount of lipid (as determined by the manufacturer). Cells were exposed to lipid:DNA complexes for four hours in serum free Ham's F-12 media, rinsed twice with PBS, and incubated in regular growth media. As shown in FIG. 5A, in all cases, transfection efficiency is higher when transfection is performed on wild-type cells that express proteoglycans relative to mutant cells that do not express significant levels of proteoglycans on the cell surface. Transfection was measured in relative light units (RLU), which correlates with luciferase expression. The ratio of luceriferase expression in wild-type cells versus mutant cells deficient in xylosyltransferase was measured as the ratio of relative light units observed following transfection of wild-type and mutant cells. Depending on the lipid formulation, the ratios ranged from 1.69 to 81, as shown in FIG. 5B.

Summary

Chlorate diminished transfection from cell surface binding, to uptake and expression of DNA. Pre-treating cells with chlorate increases transfection due to increased proteoglycan expression. Thus, the transfection efficiency of a given cell type is largely determined by membrane proteoglycan expression.

K562 cells, incapable of transfection by unmodified polysine, yield high levels of expression by transferrin-polylysine mediated gene delivery. This implies that transfection efficiency may depend more on the mechanism of entry, and less on an intrinsic, intracellular deficiency. Cell lines deficient in proteoglycan synthesis are unable to efficiently transfect polylysine:DNA, although wild-type cells yield measurable luciferase expression. These results indicate that proteoglycan expression is a rate limiting factor in transfection mediated by complexes of cationic species with genetic material, such as PLL-DNA.

Selection of Desired Genetic Material

The invention disclosed herein can employ several types of genetic material, including DNA, mRNA, RNA, PNA, modified oligonucleotides, modified polynucleotides, ribozymes and antisense oligonucleotides. In some embodiments, the genetic material is delivered to bind to or interact with a site within the cell. In those embodiments, modified oligonucleotides or polynucleotides are preferred. In those embodiments in which stable expression of a protein is desired, DNA or mRNA delivery is preferred. However, either RNA or DNA gene delivery can be used for transient gene expression applications. Without selection, it is likely that the majority of the cells will be transiently transfected. Transient expression permits gene expression for periods ranging from a few hours to several months. While repeated therapies may be required for some applications, the patient nevertheless benefits from the effect of gene expression. Like a drug, the dosage of polynucleotide and the number of delivery sites to the tissue can be monitored and adjusted accordingly.

DNA encoding a therapeutic protein may be circular or linear and should contain regulatory elements that facilitate expression in the target cells. Current progress in molecular biology is directed to identifying and isolating tissue specific promoters. As these tissue specific promoters are identified, they may be incorporated into the gene expression vector and used for ex vivo gene therapy strategies in a particular tissue. Similarly, more promiscuous promoters may be selected for a given application based on their promotional strength. For example, the actin promoter, the Rous Sarcoma virus (RSV) promoter or the Myo D promoter may be used for myoblast and muscle transfection. The cytomegalovirus (CMV) immediate early (IE) gene/enhancer (Flecking et al., Gene 45:101 (1986) hereby incorporated by reference), the RSV promoter enhancer (Wolff, J. A. et al., Science 247:1465-1468 (1990), hereby incorporated by reference), and the p-actin gene/promoter enhancer (Kawamoto et al., Mol. Cell. Biol. 8:26z (1988), hereby incorporated by reference) can be used for more ubiquitous cell expression. It is additionally contemplated that the CMV IE gene/enhancer promoter with the first intern, (Chapman, B. S. et al., Nucleic Acids Research 19:39793 (1986), hereby incorporated by reference) and the MCK promoter (Jaynes, et al., Mol. Cell. Biol. 8:62 (1988), hereby incorporated by reference) may be used for transfection in myoblasts followed by intramuscular injection for expression in mature muscle fibers. In one embodiment, the transfected DNA additionally contains regions to mediate ribosome binding, polyadenylation signals and includes enhancer regions to facilitate in vivo gene expression.

In one embodiment, RNA encoding the polypeptide of interest similarly contains appropriate promoter elements and ribosome binding sites. Preferably, the RNA is capped or stabilized to promote translation and to minimize exonuclease activity. The use of RNA in cationic-mediated gene transfer is described in a publication by Malone et al. (Proc. Natl. Acad. Sci. USA 86:6077-6081 (1989), hereby incorporated by reference).

Liposome Preparation

Liposomes are microscopic delivery vesicles formed when amphiphilic lipids are mixed with water (i.e., hydrated), and include one or more spherical lipid bilayers which surround an internal aqueous phase. Amphiphilic lipids dispersed in aqueous solution spontaneously form bilayers with the hydrocarbon tails directed inward and the polar headgroups outward to interact with water. Simple agitation of the mixture generally produces multilamellar liposomes (MLVs), structures with many bilayers in an onion-like form. MLVs typically have a mean diameter of between 1,000 to 10,000 nm. MLVs, mainly because they are relatively large, are usually taken up by the reticuloendothelial system (RES).

Unilamellar liposomes (UVs) can be formed, for example, by sonicating a dispersion of MLVs. Typical sizes of UVs range from approximately 30–1000 nm. Preferably, the liposomes used in the present invention have a mean diameter less than 200 nm.

Hydrophilic drugs can be encapsulated in the aqueous core of the vesicles, and lipophilic drugs can be dissolved in the vesicle membrane. Cationic lipids can be incorporated in liposomes and the liposomes can be complexed with polyanionic genetic material. When an excess of cationic groups to anionic groups is present, the excess cationic groups can bind to the polyanionic species on the surface of cells to which genetic material is to be added.

Selection of Lipids

Cationic lipids are amphipathic molecules, containing hydrophobic moieties such as cholesterol or alkyl side chains and a cationic group, such as an amine. Phospholipids are amphipathic molecules containing a phosphate group and fatty acid side chains. Phospholipids can have an overall negative charge, positive charge, or neutral charge, depending on various substituents present on the side chains. Typical phospholipid hydrophilic groups include phosphatidyl choline, phosphatidylglycerol, and phosphatidyl ethanolamine moieties. Typical hydrophobic groups include a variety of saturated and unsaturated fatty acid moieties.

The liposomes used in the present invention include cationic lipids that form a complex with the polyanionic genetic material and also bind to polyanionic proteoglycans present on the surface of cells. The cationic lipids can be phospholipids or lipids without phosphate groups.

Particularly preferred cationic lipids are esters of the Rosenthal Inhibitor (RI) (DL-2,3-distearoyloxypropyl (dimethyl)-β-hydroxyethylammoniumbromide), as described in U.S. Pat. No. 5,264,618, the contents of which are hereby incorporated by reference. These derivatives can be prepared, for example, by acyl and alkyl substitution of 3-dimethylaminopropane diol, followed by quaternization of the amino group. Analogous phospholipids can be similarly prepared.

Transfection efficiency can be increased by incorporating a lysophosphatide into the liposome formulation. The lysophosphatides can be present in amounts up to approximately a third of the total lipid concentration. Preferred lysophosphatides include lysophosphatidylcholines such as l-oleoyllysophosphatidylcholine and lysophosphatidylethanolamines. Particularly preferred lysophosphatides are DOTMA, 1,2-bis(oleoyloxy)3-(trimethylammonio)propane (DOTAP), Lipofectin (GIBCO/BRL, Gaithersburg, Md.) and mixtures of these.

In one embodiment, cationic lipids are used that are readily degradable in vivo. These include analogs of DORI (DL-1,2-dioleyl-3-dimethylaminopropyl-β-hydroxyethylammonium) and DORIE (DL1,2-O-dioleyl-3dimethylaminopropyl-β-hydroxyethylammonium) as well as DORI ester/ether compounds (DL-1-O-oleyl-2-oleyl-3-dimethylaminopropyl-β-hydroxyethylammonium or DL-1-oleyl-2-O oleyl-3-dimethyl-aminopropyl-β-hydroxyethylammonium).

Liposomes can be stabilized by incorporating a neutral lipid, such as cholesterol, into the liposome formulation. Typically, a mole ratio of between approximately 4:1 and 55:45 lipid to cholesterol, and, preferably, approximately 2:1 lipid to cholesterol will provide liposomes that are stable.

Neutral phospholipids such as DOPE, DOPC, DMPC, and DPPC can also be added. The ratios of lipids may vary to include a majority of cationic lipid in combination with cholesterol and/or mixtures of lyso or other neutral lipids.

Liposomal Targeting

The liposomes of the present invention can be targeted through various means. The size of the liposome provides one means for targeting the liposomes. For example, relatively small UVs efficiently target ischemic tissue and tumor tissue, as described in U.S. Pat. No. 5,527,538, and U.S. Pat. Nos. 5,019,369, 5,435,989 and 5,441,745 to Presant et al., the contents of which are hereby incorporated by reference.

The liposomes can be targeted according to the mode of administration. For example, lung tissue can be targeted by intranasal administration, cervical cells can be targeted by intravaginal administration, and prostate tumors can be targeted by intrarectal administration. Skin cancer can be targeted by topical administration. Depending on location, tumors can be targeted by injection into the tumor mass.

Further, liposomes can be targeted by incorporating a ligand such as an antibody, a receptor, or other compound known to target liposomes to various sites, into the liposomal formulation. The ligands can be attached to cationic lipids used to form the liposomes, or to a neutral lipid such as cholesterol used to stabilize the liposome. Ligands that are specific for one or more specific cellular receptor sites are attached to a vesicle to form a delivery vehicle that can be targeted with a high degree of specificity to a target cell population of interest.

Suitable ligands for use in the present invention include, but are not limited to, sugars, proteins such as antibodies, hormones, lectins, major histocompatibility complex (MHC), and oligonucleotides that bind to or interact with a specific site. An important criteria for selecting an appropriate ligand is that the ligand is specific and is suitably bound to the surface of the vesicles in a manner which preserves the specificity. For example, the ligand can be covalently linked to the lipids used to prepare the liposomes. Alternatively, the ligand can be covalently bound to cholesterol or another neutral lipid, where the ligand-modified cholesterol is used to stabilize the lipid bilayer.

Cytokines are preferred ligands. IL-2 is a preferred cytokine. This ligand is particularly useful for targeting specific activated T- and B-cell populations in view of the particular specificity for the high affinity IL-2 receptors on such cells. The IL-2 ligand can be stabilized for in vivo use by certain amino acid substitutions, as described in Wang and Mark, *Science* 224:1431 (1984). Other suitable cytokines for use as ligands in the present invention include, but are not limited to, antigrowth factors, B cell growth factors, chalcones, chemotactic factors, colony stimulating factor, GM-CSF, G-CSF, growth factors, interferon alpha and beta, interleukin-1 alpha and beta, Interleukins 1-6, lymphotoxin, tumor necrosis factor, macrophage inhibitory factors, and T-cell replacing factor.

Some lipids already include ligands that are suitable for targeting various cell types. These include glycolipids, lipoproteins, glycoproteins, and hydrophobic proteins. Examples described in the literature include gangliosides (Jonah, et al., *Biochem. Biophys. Acta* 541:321 (1978)), lactosyl ceramide (Spanjer and Scherphof, *Biochem. Biophys. Acta*, 734:40 (1983)), and sialoglycoprotein (Takada et al., *Biochem. Biophys. Acta*, 802:237 (1984). Synthetic cholesterol derivatives covalently bound to sugars such as aminomannose have been described, for example, in Mauk, et al., *Science* 207:309 (1980). Vesicles including aminomannose derived cholesterol have been demonstrated to target EmT6 tumor cells. These compounds can be incorporated into the lipid bilayer when the liposomes are prepared. Dinitrophenyl caproylphosphatidylethanolamine and other phosphatidylethanolamine derivatives linking small peptides have also been directly incorporated into lipid bilayers. Proteins have been covalently linked to liposomes through thiol, hydroxy and/or amine groups on the protein and the lipid, using known coupling techniques, for example, carbodiimide or glutaraldehyde chemistry.

It is preferred that the ligand be covalently bound to the surface of a preformed lipid vesicle, to ensure that the ligand is present on the outside of the vesicle. The binding can occur directly or through a suitable linker molecule.

In Vitro Transfection

When transfection is performed in vitro, cells to be transfected are contacted with an effective amount of a formulation that includes an effective amount of a complex of a cationic species and genetic material to effectively transfect all or a portion of the cells, and an effective amount of a material known to increase the expression of proteoglycans on the cell surface. Transfection efficiency can be measured by using the techniques disclosed below in Example 4.

Ex Vivo Transfection

Ex vivo transfection requires first removing tissue or a cell sample from an organism. The organism is preferably a mammal, and more preferably, a human. The cells are then contacted with a preparation including an effective amount of a complex of the desired genetic material and a cationic species, together with an effective amount of a compound that increases expression of proteoglycans on the cell surface. Following transfection, the cells are returned to the organism. Preferably, the cells are returned within less than 40 hours after removing the sample from the organism. The procedure delivers a genetic material, preferably material that operatively codes for a polypeptide to the interior of the transfected cell.

In one embodiment, after the cells are removed, they are substantially separated from the surrounding extracellular tissue before they are contacted with the preparation. As one example of a cell separation method, a skin biopsy is enzymatically digested to dissociate the cells from their extracellular matrix.

Preferably, the cells are isolated, exposed to the gene of interest, and returned directly to the host with minimal time in culture to reduce the potential for cell change in vitro. Some of the cells express the desired gene transiently, others stably; however, with a minimum turn around time, the cells are more likely to survive in vivo. Whether stable or transient expression is achieved, the result is beneficial. If needed, the therapy can be repeated to maintain the desired level of exogenous gene expression. The methods discussed herein teach one of skill in the art to introduce gene sequences such that a variety of cells from a variety of tissues can be treated ex vivo and rapidly returned to a host for gene expression without selection for stable transfectants.

Biopsy and Tissue Processing

A biopsy or cell sample is preferably obtained from a patient in need of gene therapy. Alternatively, the treated cells can be derived from a secondary source such as a cell line or a cell donor. The cell sample is preferably obtained from a tissue where gene expression would be most advantageous. The cell sample may be derived from a variety of tissues, including, but not limited to, skin, liver, pancreas, spleen, muscle, bone marrow, nervous system cells, blood cells, and tumor cells.

The type of tissue and location of that tissue will suggest the best method of tissue sampling. Those with skill in the art will readily appreciate the variety of biopsy and sampling procedures available for a given tissue type. Biopsy of formed tissue may be obtained by needle, catheter, punch biopsy or surgical excision. For example, a skin biopsy may be best obtained by a skin punch, while a liver biopsy may be best obtained by a needle biopsy.

For cell types present in the blood, a simple blood draw into a heparinized, EDTA, or citrate tube can be processed by centrifuging at 1000 rpm for 10 min. The cells can then be washed to remove serum, red blood cells, and debris, and then used directly.

Biopsies removed from a patient are preferably placed in sterile saline and washed to remove blood and debris. The tissue is then preferably minced with a scalpel or single edge razor blade until the tissue resembles a thick paste. The mincing is preferably performed in a small amount of Hanks Balanced Salt Solution (GIBCO, Grand Island, N.Y.) or other suitable solution that permits the relative pH of the tissue sample to be monitored during processing, because maintaining physiologic pH is important to cell survival.

The paste can then be treated with an enzyme preparation such as trypsin and collagenase B (Boehringer Mannheim, Indianapolis, Ind.), and also treated to remove connective tissue fragments. Other enzymes used in tissue dissociation include Versene, pancreatin and other collagenases. The enzymatic solution is the preferably washed away from cell suspension, and the cells are washed and then used for transfection.

For some gene therapy applications, a uniform cell population is preferred. In these applications, the cells are first dissociated and then separated from other cell types. There are a variety of methods known to those with skill in the art for removing a particular cell type from a mixed suspension of cells.

Cell types can be differentiated from one another by their density or size. For example, mesh screens or sucrose gradient centrifugation can be used to separate one cell population from another. Cells can additionally be separated on the basis of their adherent properties. For example, fibroblasts will adhere and settle onto plastic more quickly than epithelial cells. Populations of cells can also be separated from one another by virtue of surface protein. Lectins or antibodies can be used to selectively separate one population of cells from another either using panning (passing cells over a surface with bound lectin or antibody), column chromatography or fluorescent activated cell sorting. According to a preferred method, cells from a blood sample are separated in a device (The Collector, Applied Immune Sciences, Menlo Park, Calif.) which includes multiple polystyrene plates to which monoclonal antibodies, which bind selectively to specific cells, have been permanently attached. When a blood sample is processed in The Collector, targeted cells remain attached to the polystyrene surface, while other cells pass through the device. The captured cells can then be released by mechanical or chemical means. Those with skill in the art will be able to select the appropriate cell separation method for their particular application.

The washed and dissociated cells can be stored for up to 24 hours or longer in culture. However, the cells are preferably transfected immediately following tissue dissociation and cell purification. If there is a delay between cell isolation and transfection it is worthwhile to return the cells to a nutritive environment. The cells can be stored in tissue culture medium with a composition compatible to the particular cell type. Typically Eagles (EMEM) or Dulbecco's minimum essential medium (DMEM) and an antibiotic solution (Fungi Bact Solution, Irvine Scientific, Irvine, Calif.; that contains penicillin, streptomycin and fungizone) are used to maintain the cells ex vivo.

Optionally, ex vivo transfection can include a selection step to separate or expand the transfected cells. Transfected cells can be frozen for storage prior to re-insertion into the organism. In one embodiment, the genetic material is added to bind to or interact with a site within the cell. In another embodiment, the genetic material encodes a peptide that is adapted to treat a disease caused by a functional gene deficiency. In this embodiment, it is preferred that the genetic material expresses the polypeptide in the live cells. The expression of the polynucleotide by the cells may be transient, or may persist for a substantial length of time. In one preferred embodiment, the polypeptide is an immunogenic polypeptide in the organism. In such a case, the organism (preferably a mammal, more preferably a human) develops an immune response against the immunogen after the transfected cells are reintroduced. This method may be used to immunize the organism. In one preferred embodiment, the operatively linked genetic material codes for a lymphokine. Cells that may be used include, but are not limited to, white blood cells, myoblasts, and bone marrow cells.

There are a variety of tissue dissociation methods available along with different cell purification schemes. Biopsies and cells may be frozen before or after tissue dissociation. Dissociation and purification procedures should be performed as rapidly and expediently as possible after biopsy to maximize cell viability. Once dissociated, the cells are transfected. The transfected cells are preferably returned immediately to the patient without expansion or selection in culture. For some applications the biopsied tissue can be dissociated, treated with the desired genetic material, and frozen without expansion or selection in culture. Samples can be thawed as necessary for future treatments. Similarly, a portion of the frozen cells can be thawed and assayed for transfection efficiency or for gene expression. There are a variety of methods known to those with skill in the art for freezing cells.

A muscle biopsy can be used to isolate muscle myoblasts. Patient myoblasts can be isolated following the techniques of Blau et al. (*Proc. Natl. Acad. Sci. USA* 78:5623–5627, 1981, the contents of which are hereby incorporated by reference). Myoblasts are readily obtained from muscle without substantial inconvenience to the patient. A small amount of tissue, processed according to the techniques of Blau et al., yields sufficient quantities of myoblasts for transfection. The muscle myoblasts are then transfected ex vivo following the methods disclosed herein and returned to the muscle or to other tissues of the patient. Myoblasts can additionally be stored or frozen for a time without a significant loss in cell viability or a significant change in cell phenotype.

When myoblasts are reintroduced back into muscle, they are capable of fusing with the available mature myofibers. Accordingly, myoblast delivery is a particularly efficient method for gene delivery to muscle cells. Since the myoblasts are readily isolated and conveniently obtained from muscle tissue of the patient, there is no risk of tissue rejection. Transient gene expression is more likely to be sustained over time from repeated therapies in autologous cells. Another important advantage to myoblast transfection is that muscle tissue is accessible to injection and underlies most surfaces of the body, thus the transfected cells can be injected in multiple locations as often as needed. Using muscle specific promoters like MCK, gene product expression can be restricted to mature muscle fibers. The muscle cells thus express the desired polynucleotide sequence. Recent work indicates that stable myoblast transfectants injected into muscle tissue express their gene product into the blood stream (Hoffman, M. Science 254:1455–1456, 1991).

Reintroduction of treated cells

Once transfection is complete, the cells are washed, concentrated and returned to the patient. The cells may be returned directly to their tissue of origin, or for some applications, the cells can be returned to a second location either within the tissue of origin or at a location distant from the tissue of origin. A large bore needle (18 gauge or larger) is preferably used to return cells to the body. Any bore size may be used that does not destroy the cells or restrict cell passage into the tissue. It may be beneficial to introduce the treated cells into multiple locations within a given tissue. For example, in treating Duchenne's muscular dystrophy, multiple injections of treated cells will advantageously disperse the gene product throughout the tissue.

If transfection occurs without tissue dissociation, the intact biopsy can be replaced by surgical implantation. Other cells, such as hepatocytes, can be administered to their organ of origin by injecting them into a vein that leads to the organ.

Methods to return treated cancer cells to a patient will depend on the cancer type. One can inject autologous transfected cancer cells into either a tumor mass or bone marrow. One can stimulate immune responses directed to both the treated and untreated tumor cells, thereby reducing or clearing the tumor mass, by expressing an MHC protein, a foreign protein or an immune stimulating protein. Other transfected cancer cells of hematopoietic origin may be introduced directly into the blood stream. Cells from hard tissue tumors may be replaced directly into a tumor mass to elicit tumor regression through external injection or internal injection using catheters or the like.

There are a variety of alternative techniques and procedures available to those of skill in the art which would similarly permit one to successfully perform the intended invention.

In Vivo Transfection

When transfection is performed in vivo, glycosaminoglycans in the plasma can adversely affect the transfection efficiency. Transfection efficiency can be increased by lowering the plasma concentration of glycosaminoglycans and, optionally, other polyanionic species, and can be lowered by increasing the plasma concentrations of glycosaminoglycans.

Transfection can be performed in vivo by administering an effective amount of the complex to cause transfection of a significant amount of the cells and an effective amount of compounds that increase proteoglycan expression on the cell surface, and, optionally, compounds that decrease the plasma concentration of glycosaminoglycans. The complex and the compounds can be administered at the same time or within a reasonable time of each other, so long as the overall effect is that the cell surface concentration of proteoglycans increases and/or the plasma concentration of glycosaminoglycans decreases when transfection occurs.

Preferably, the cationic species used to prepare the complex is a cationic liposome. More preferably, the liposome is prepared to specifically target a certain cell type. For example, certain antibodies are known to target liposomes to various cells. By using unilamellar vesicles less than 200 nm in diameter, tumor cells can be targeted for transfection. By administering the liposomes intranasally via an aerosol, lung tissue can be targeted.

Minimizing Transfection Efficiency

The understanding of the role of proteoglycans in transfection also allows minimization of transfection efficiency. Minimizing transfection efficiency can be important in preventing or minimizing viral infections, in embodiments in which viral DNA infects cells by first binding to polyanionic sites on the cell surface, rather than to other cell receptors. To minimize viral infection, the amount of proteoglycans on the cell surface can be reduced, and/or the concentration of proteoglycans or other polyanionic substances in the plasma can be increased. The amount of proteoglycans on the cell surface can be minimized by adding various compounds that are known to lower the concentration of proteoglycans.

The interaction of the viral DNA with the cell surface can also be minimized by increasing the plasma concentration of proteoglycans and/or other polyanionic species. The concentration of these species can be increased by directly adding the polyanionic species to the plasma, and/or by adding an effective amount of one or more substances known to increase the plasma concentration of these species.

Methods for minimizing transfection efficiency can also be used to target cells in which transfection is not desired, by lowering the proteoglycan expression on the surface of those cells, and then introducing genetic material to cells in which transfection is desired.

For example, targeted administration of sodium chlorate to specific cells can effectively diminish the cell surface concentration of proteoglycans, and thus minimize transfection efficiency in the targeted cells. General administration of chlorate ions will generally reduce the efficiency of transfection.

Controlling Transfection Efficiency by Controlling the Ratio of Various Types of Proteoglycans on the Cell Surface Transfection efficiency can also be controlled by modifying proteoglycan expression such that the cells express a different ratio of different types of proteoglycans on the cell surface. In some cases, higher concentrations of chondroitan-based proteoglycans on the surface of cells causes increased transfection efficiency, whereas in others, higher concentrations of heparan sulfate-based proteoglycans on the surface of cells causes increased transfection efficiency. One of skill in the art can readily determine which proteoglycans are preferred. Methods for modulating the ratio of heparan sulfate to chondroitin sulfate using glycosaminoglycan biosynthesis inhibitors is known in the art, as described by Timar, J. et al. in *Int. J. Cancer*, 62:755–761 (1995). Suitable glycosaminoglycan biosynthesis inhibitors for use in the present invention include, but are not limited to, β-D-xyloside, 2-deoxy-D-glucose, ethane-1-hydroxy-1, 1-diphosphonate and 5-hexyl-2-deoxyuridine.

Improved Cationic Liposomes

Transfection efficiency can be increased by complexing genetic material with a cationic lipid that is covalently or ionically bound to an agent known to increase the amount of proteoglycans on the cell surface. Alternatively, neutral lipids, lysolipids and neutral phospholipids can be covalently or ionically bound to an agent known to increase the amount of proteoglycans on the cell surface, and these modified lipids can be included in a cationic liposome formulation. Cationic liposomes prepared from the resulting lipids also increase transfection efficiency by increasing the concentration of cell surface proteoglycans.

For example, phorbol esters such as TPA and PMA can be reacted with a suitable lipid with one or more hydroxy or amine groups to form an ester or amide linkage. Anabolic cytokines with reactive functional groups can be similarly coupled to suitable lipids using known chemistry.

Alternatively, lipids covalently or ionically linked with substances known to decrease the cell surface expression of proteoglycans can be administered to those cells in which transfection is not desired, before a complex of genetic material and a cationic species is administered to cells in which transfection is desired. For example, xylosides or catabolic cytokines with reactive functional groups can be covalently linked to suitably functionalized lipids to prepare modified lipids that reduce the cell surface expression of proteoglycans.

Cytokines, whether anabolic, catabolic or modulatory, can be covalently linked to these lipids to form compounds that increase, decrease or otherwise modulate expression of proteoglycans on the cell surface.

Transfection of Non-Differentiated Cells and Cancer Cells

In another embodiment, the efficiency of transfection of non-differentiated cells can be increased by causing the non-differentiated cells to express proteoglycans at or near the time the cells are transfected. Transfection of non-differentiated cells can be important where a genetic defect is present in the cells, which defect can be corrected before the cells become differentiated. After a cell differentiates, it is often difficult to correct the genetic defect.

In this embodiment, the genetic material is preferably administered directly to the developing fetus. Several genetic defects have been characterized, and an appropriate genetic "splice" has been identified. It is expected that, over time, additional genetic defects will be characterized. However, due to the low concentration of proteoglycans on the cell surface, non-differentiated cells have been difficult to transfect. The present method increases the transfection efficiency, allowing more efficient gene replacement for correcting genetic defects.

Cancer cells also exhibit low cell surface contentrations of proteoglycans. Although these cells can be transfected, the transfection efficiency can be increased by increasing the cell surface concentration of proteoglycans.

EXAMPLES

The following examples are given to explain and illustrate the present invention and are not to be taken as limiting the invention.

Materials and Methods

Cell Culture

HeLa cells were obtained from the American Type Culture Collection and grown in Dulbecco's Modified Eagles Media (DMEM, Gibco) containing Basal Medium Eagle Amino Acids (Gibco), Non-essential Amino Acids (Gibco), 10% fetal bovine serum (Hyclone), and 40 mg/ml gentamicin (Gibco).

Mutant (CHO-pgs 745) and wild-type (CHO-K1) cells were generously donated by Dr. J. D. Esko (University of Alabama, Birmingham, School of Medicine). The mutant cell line lacks xylosyltransferase, an initiator of glycosaminoglycan synthesis, and makes little if any glycosaminoglycan. Both cell lines were proliferated in Ham's F-12 media, 7.5% FBS and subcultured every four days.

For all cell types, transfection media consisted of regular growth media supplemented with 100 μM chloroquine (Sigma).

Example 1

Preparation of Fluorescent and Nick Translated Plasmids

The PGL2 plasmid (Promega) encoding the firefly luciferase reporter gene was amplified in competent JM109

*Escherichia Coli* (Promega) and purified by chromatographic methods (Qiagen).

DNA (1.5 mg) was labeled with a-$^{32}$PdCTP (3000 Ci/mmol) using a Nick Translation Kit (Boehringer Mannhiem) and purified by repeated chloroform: phenol extractions and ethanol precipitation. A stock solution of DNA was prepared by mixing nick translated plasmid with approximately 80 mg unlabelled DNA. The concentration of DNA was determined by UV-Vis analysis (max=260 nm).

To prepare fluorescent DNA, plasmid (100 mg/ml) was incubated with a fifty-fold molar excess of YOYO-1 (Molecular Probes), a highly fluorescent DNA intercalator, and incubated for two hours at 4° C. The solution was loaded onto a Centricon-30 desalting unit and spun for 3 hours at 6000 rpm and 4° C. to remove unbound YOYO. The retentate was diluted to its original concentration in sterile water. The concentration of YOYO per mole plasmid was determined by UV-Vis analysis. The fluorescence of YOYO-DNA (YYDNA) was monitored through excitation fluorimetry (lex=488 nm, lem=512) in a Hitachi model 7650L fluorimeter.

Example 2

Desulfation of Cells

HeLa cells (20K cells/ml) were seeded into 12 well plates (Falcon). Twelve hours later, media was supplemented with sodium chlorate (Aldrich, 35 mM) or a combination of sodium sulfate (Baker, 80 mM) and sodium chlorate (35 mM). Following an additional 48 hour incubation period, cells were rinsed twice with 1 ml PBS and placed into 1 ml transfection media. Transfection, fluorescence uptake, or binding experiments immediately followed. Cultures were approximately 70% confluent.

Example 3

Treatment of cells with Glycosaminoglycan Lyases and Purified Glycosaminoglycans HeLa cells were seeded at a density of 50K/ml into 12 well plates (Falcon). Eighteen hours later, cells were rinsed twice with 1 ml PBS and placed into a BSA/Locke solution containing either 10 units/ml chondroitinase ABC (Sigma) or heparinase 11 (Sigma). Cells were incubated with lyases for one hour at 37° C. Following the enzymatic digestion of surface glycosaminoglycans, cells were rinsed twice with PBS and transfected according to the normal protocol.

To evaluate the effect of free glycosaminoglycans on transfection, DNA complexes and glycosaminoglycans (40 mg/ml, either heparan sulfate, heparan, chondroitan sulfate A, chondroitan sulfate B, chondroitan sulfate C, or hyaluronic acid) were added together at the time of transfection. Transfected cells were treated as per the normal protocol.

Example 4

Preparation of Complexes and Transfections

An aliquot of poly-L-lysine (100 mg/ml, Sigma) was added to DNA (1.5 mg, 100 mg/ml) diluted in 150 ml HBS (Hepes Buffered Saline, 150 mM, pH 7.4). Polylysine-DNA (PLL-DNA) samples were mixed gently, incubated for 30 minutes at room temperature, and added to cells in the presence of transfection media. Four hours later, cells were rinsed twice in 1 ml phosphate buffered saline (PBS, 150 mM NaCl, 150 mM NaHPO$_3$, pH 7.4) and placed into fresh culture media at 37° C. Following an additional 21 hour incubation at 37° C, the media was removed and cells were rinsed twice in 2 ml PBS. Luciferase expression in cellular lysates was determined using an Enhanced Luciferase Assay Kit (Analytical Luminescence Laboratories) according to the manufacturer's instructions. Expression was quantitated in terms of Relative Light Units (RLU) on an Analytical Luminescence Laboratories Model 2010 Luminometer.

Example 5

Florescence Uptake Experiments and Confocal Microscopy

HeLa, CHO-pgs 745, and CHO-K1 cells were incubated with PLL-YYDNA for four hours and then rinsed three times in PBS. To remove surface bound DNA, cells were treated with DNAse (Sigma, 1 mg/ml) for 15 minutes and then detached by trypsin. Cell suspensions were pelleted, washed twice in PBS, and fixed in 4% paraformaldehyde/PBS for 10 minutes at room temperature. After a final rinse in PBS, cell pellets were resuspended in Biomeda/PBS solution (90:10) and mounted between a slide and coverslip to dry. Fluorescence images were obtained using a BioRad Confocal Microscope.

The invention has been described with respect to its preferred embodiments. It will be readily apparent to those skilled in the art that further changes and modifications in the actual implementation of the concepts described herein can easily be made without departing from the spirit and scope of the invention as defined by the following claims.

We claim:

1. A method for administering genetic material to cells, comprising administering to the cells an effective amount of a complex of genetic material and a cationic species and an effective amount of a compound that increases proteoglycan expression on the cell surface to increase the transfection efficiency relative to when the cells exhibit normal proteoglycan expression, wherein the genetic material is administered in vitro, in vivo, or ex vivo.

2. The method of claim 1, wherein the cationic species is selected from the group consisting of cationic lipids, cationic liposomes, calcium ions, lipopolyamine, polyethylene imine, polycationic amphiphiles, DEAE-dextran and dendrite polymers containing cationic functional groups.

3. The method of claim 1, wherein the cationic species is a cationic lipid or a cationic liposome.

4. The method of claim 3, wherein the cationic liposomes include lyso lipids, cholesterol, or neutral phospholipids.

5. The method of claim 1, wherein the ratio by charge of cationic species to genetic material is between approximately 1.5 and 6.

6. The method of claim 3, wherein the liposomes comprise a lipid bound to a ligand, wherein the lipid is selected from the group consisting of neutral phospholipids, cationic phospholipids, cationic lipids, neutral lipids, and lysolipids, and wherein the ligand is selected from the group consisting of sugars, proteins, hormones, cytokines, lectins, major histocompatibility complex (MHC) and oligonucleotides that bind to or interact with a specific site.

7. The method of claim 1, wherein the genetic material is selected from the group consisting of DNA, RNA, mRNA, ribozymes, antisense oligonucleotides, modified polynucleotides, modified oligonucleotides, and combinations thereof.

8. The method of claim 1, wherein the cells to be transfected are selected from the group consisting of fibroblasts, myoblasts, hepatocytes, cells of hematopoetic origin, cancer cells, ischemic tissue, cells neurons and other cells of the nervous system and non-differentiated cells.

9. The method of claim 1, wherein the cells to be transfected are non-differentiated cells or cancer cells.

10. The method of claim 1, wherein the compound that increases proteoglycan expression is selected from the group consisting of phorbol esters, EGF, IGF-1, IL-3, IL-5, FGF, Interferon, PDGF, and TGF beta.

11. The method of claim 1, wherein the compound that increases proteoglycan expression is selected from the group consisting of phorbol esters, FGF, Interferon, PDGF, and TGF beta.

12. The method of claim 11, wherein the phorbol ester is TPA or PMA.

13. The method of claim 1, wherein said transfected genetic material is transiently expressed.

14. The method of claim 1, wherein said transfected genetic material is stably expressed.

15. The method of claim 1 performed in the presence of plasma, and further comprising administering an effective amount of a compound that reduces the plasma concentration of glycosaminoglycans to increase the efficiency of transfection relative to when the plasma exhibits normal glycosaminoglycan concentrations, wherein the compound that reduces the plasma concentration of glycosaminoglycans is selected from the group consisting of protease inhibitors, plasma lipoproteins, growth factors, lipolytic enzymes, extracellular matrix proteins and platelet factor 4.

16. The method of claim 15, wherein the compound that reduces the plasma concentration of glycosaminoglycans is selected from the group consisting of protease inhibitors and plasma lipoproteins.

17. The method of claim 15, wherein the compound that reduces the plasma concentration of glycosaminoglycans is a protease inhibitor.

18. The method of claim 1, wherein the transfection is performed in vitro or ex vivo, further comprising a selection step to separate or expand the transfected cells.

19. The method of claim 1, wherein the genetic material encodes a polypeptide that is adapted to treat a disease caused by a functional gene deficiency.

20. The method of claim 19, wherein the polypeptide is an immunogenic polypeptide.

21. The method of claim 1, wherein the genetic material operatively codes for a lymphokine.

22. The method of claim 1, wherein liver cells are transfected with the LDL receptor to reduce serum cholesterol in vivo.

23. The method of claim 1, wherein progenitor cells from the hematopoietic system are treated at a predifferentiated stage to correct hereditary disorders.

24. The method of claim 1 wherein the genetic material operatively codes for interferon and cytokines are administered to stimulate the immune system to react against foreign antigens or cancers.

25. The method of claim 1, wherein the genetic material encodes a protein that stimulates the immune system to recognize a given population of cancer cells as foreign.

26. The method of claim 1, wherein the genetic material renders cancer cells chemosensitive.

27. The method of claim 1, further comprising administering an additional therapeutic agent to the cells.

28. The method of claim 27, wherein the therapeutic agent is selected from the group consisting of cytotoxic agents, antifungal agents, antibacterial agents, antiviral agents, immunomodulating agents, anti-inflammatory agents, vasoconstrictors and vasodilators.

29. The method of claim 1, wherein the transfection is performed in vivo, and wherein the complex is administered via a mode of administration selected from the group consisting of oral, parenteral, intravenous, intramuscular, intraperitoneal, intranasal, and intrauteral.

30. The method of claim 1, wherein the transfection is performed in vivo, and wherein lung tissue is targeted for transfection by administering the complex intranasally via an aerosol.

31. The method of claim 1, wherein the complex further includes an antibody or a receptor.

32. The method of claim 1, wherein the cells to be transfected are mammalian.

33. The method of claim 1, wherein the cells to be transfected are human.

34. A method for decreasing the efficiency of administration of complexes of genetic material and cationic species to cells comprising reducing the amount of proteoglycans on the cell surface by administering an effective amount of a compound that reduces the expression of proteoglycans on the cell surface, wherein the compound is selected from the group consisting of protease inhibitors, plasma lipoproteins, growth factors, lipolytic enzymes, extracellular matrix proteins, platelet factor 4, IL-1 alpha and beta, and TNF-alpha, wherein the transfection is performed in vitro, in vivo or ex vivo.

35. The method of claim 34, wherein the compound is selected from the group consisting of protease inhibitors, plasma lipoproteins, growth factors, lipolytic enzymes, extracellular matrix proteins, and platelet factor 4.

36. A method for decreasing the efficiency of transfection performed in the presence of polyanionic species in the plasma, comprising administering, before transfection occurs, an effective amount of glycosaminoglycans or other polyanionic species to decrease the transfection efficiency relative to where transfection occurs in the presence of a normal plasma concentration of glycosaminoglycans and other polyanionic species.

37. The method of claim 3, wherein the cationic lipid is selected from the group consisting of DOTMA (N-[1-(2,3-dioleyloxy)propyl]-N,N,N-trimethylammonium), Lipofectin, 1,2-bis(oleoyloxy)-3-(trimethylammonio) propane (DOTAP), N-(w,w-1-dialkoxy)-alkyl-N,N,N-trisubstituted ammonium surfactants, DORI (DL-1,2-dioleoyl-3-dimethylaminopropyl-β-hydroxyethylammonium), DORIE (DL-1,2-O-dioleyl-3-dimethylaminopropyl-β-hydroxyethylammonium), DORI ester/ether compounds (DL-1-O-oleyl-2-oleoyl-3-dimethylaminopropyl-β-hydroxyethylammonium, DL-1-oleoyl-2-O-oleyl-3-dimethylaminopropyl-β-hydroxyethylammonium) and mixtures thereof.

* * * * *

UNITED STATES PATENT AND TRADEMARK OFFICE
CERTIFICATE OF CORRECTION

PATENT NO. : 5,783,566
DATED : July 21, 1998
INVENTOR(S) : Kimberly Mislick

It is certified that error appears in the above-identified patent and that said Letters Patent is hereby corrected as shown below:

Column 1, Line 5, please insert at the beginning
--The U.S. Government has certain rights in this invention pursuant to Grant No. GM 08346 awarded by the National Institute of Health.--

Signed and Sealed this

Twenty-seventh Day of July, 1999

*Attest:*

Q. TODD DICKINSON

*Attesting Officer*     *Acting Commissioner of Patents and Trademarks*